US005534615A

United States Patent [19]
Baker et al.

[11] Patent Number: 5,534,615
[45] Date of Patent: Jul. 9, 1996

[54] CARDIAC HYPERTROPHY FACTOR AND USES THEREFOR

[75] Inventors: Joffre Baker, El Granada; Kenneth Chien, La Jolla; Kathleen King, Pacifica; Diane Pennice, Burlingame; William Wood, San Mateo, all of Calif.

[73] Assignees: Genentech, Inc., South San Francisco; The Regents of the University of California, Oakland, both of Calif.

[21] Appl. No.: 233,609

[22] Filed: Apr. 25, 1994

[51] Int. Cl.$^6$ ............................ C07K 1/00; A61K 35/14; A61K 35/30
[52] U.S. Cl. ........................ 530/350; 530/380; 424/569; 424/570
[58] Field of Search .................................. 530/350, 380; 424/569, 570

[56] References Cited

U.S. PATENT DOCUMENTS

| | | | |
|---|---|---|---|
| 4,339,441 | 7/1982 | Kalman et al. | 424/177.1 |
| 4,900,811 | 2/1990 | Sutcliffe | 530/324 |
| 4,923,696 | 5/1990 | Appel et al. | 424/548 |
| 5,107,375 | 5/1991 | Appel et al. | 424/570 |
| 5,166,317 | 11/1992 | Wallace et al. | 530/350 |
| 5,202,428 | 4/1993 | Schubert | 435/320.1 |
| 5,206,007 | 4/1993 | Ooshima et al. | 424/9 |
| 5,210,026 | 5/1993 | Kovesdi et al. | 435/69.1 |
| 5,214,031 | 5/1993 | Uchida | 514/12 |
| 5,215,969 | 6/1993 | Springer et al. | 514/21 |
| 5,218,094 | 6/1993 | della Valle | 530/417 |
| 5,242,798 | 9/1993 | Sutcliffe | 435/7.1 |
| 5,250,414 | 10/1993 | Schwab et al. | 435/7.72 |
| 5,284,932 | 2/1994 | Sen | 530/324 |

FOREIGN PATENT DOCUMENTS

| | | |
|---|---|---|
| 0233838A2 | 8/1987 | European Pat. Off. |
| 0476933A1 | 3/1992 | European Pat. Off. |
| 0474979A1 | 3/1992 | European Pat. Off. |
| 55020721A | 2/1980 | Japan |
| 4169600A | 6/1992 | Japan |
| WO90/09399 | 8/1990 | WIPO |
| WO92/11026 | 7/1992 | WIPO |
| WO92/18140 | 10/1992 | WIPO |
| WO92/20797 | 11/1992 | WIPO |
| WO92/22665 | 12/1992 | WIPO |
| WO93/03758 | 3/1993 | WIPO |
| WO93/06116 | 4/1993 | WIPO |
| WO93/07270 | 4/1993 | WIPO |
| WO93/18065 | 9/1993 | WIPO |
| WO93/24529 | 12/1993 | WIPO |
| WO94/05788 | 3/1994 | WIPO |

OTHER PUBLICATIONS

Chien, "Molecular Advances in Cardiovascular Biology" *Science* 260:916–917 (May 14, 1993).

Jones et al., "Association Between Inhibition of Arachidonic Adic Release and Prevention of Calcium Loading During ATP Depletion in Cultured Rat Cardiac Myocytes" *American Journal of Pathology* 135(3):541–556 (1989).

Miller–Hance et al., "In Vitro Chamber Specification During Embroyonic Stem Cell Cardiogenesis" *The Journal of Biological Chemistry* 268(33):25244–25252 (Nov. 25, 1993).

Pennica et al., "Expression Cloning of Cardiotrophin 1, a Cytokine That Induces Cardiac Myocyte Hypertrophy" *Proceedings of the National Academy of Sciences, USA* 92:1142–1146 (Feb. 1995).

Bazan, "Neuropoietic Cytokines in the Hematopoietic Fold", *Neuron*, 7:197–208, (1991).

Boheler et al., "Gene Expression in Cardiac Hypertrophy", *TCM*, 2(5):176–182, (1992).

Chen et al., "Pharmacological Characterization of the Activity of Endogenous Inotropic Factor from Porcine Left Ventricle", *J. Cardiovas. Pharmacol.*, 22(Suppl. 2):S93–S95, (1993).

Chien et al., "Transcriptional Regulation During Cardiac Growth and Development", *Annu. Rev. Physiol.*, 55:77–95, (1993).

Chien et al., "Regulation of Cardiac Gene Expression During Myocardial Growth and Hypertrophy: Molecular Studies of an Adaptive Physiologic Response", *The FASEB J.*, 5:3037–3046, (1991).

Davis et al., "The Molecular Biology of the CNTF Receptor", *Curr. Opin. Cell Biol.*, 5:281–285, (1993).

Frelin, "Serum Growth Factors for Rat Cardiac Non–Muscle Cells in Culture", *J. Molec. and Cell. Cardiol.*, 12:1329–1340, (1980).

Grimm et al., "Ventricular Nucleic Acid and Protein Levels with Myocardial Growth and Hypertrophy",*Cir., Res., XIX*:552–558, (1966).

Iwaki et al., "α–and β–Adrenergic Stimulation Induces Distinct Patterns of Immediate Early Gene Expression in Neonatal Rat Myocardial Cells", *J. Biol. Chem.*, 265(23):13809∝13817 (1990).

Kanda et al., "An Interleukin–6 Secreting Myxoma in a Hypertrophic Left Ventricle", *Chest*, 105(3):962–963, (1994).

Karasik et al., "Growth Factors Identified in Myocardium of Patients with Hypertrophic Cardiomyopathy", Abstract, *JACC,* 13(2):118A, (1989).

Kishimoto et al., "Cytokine Signal Transduction", *Cell*, 76:253–262, (1994).

Kitamura et al., "Multimeric Cytokine Receptors", *TEM*, 5(1):8–14, (1994).

(List continued on next page.)

*Primary Examiner*—Robert A. Wax
*Assistant Examiner*—Hyosuk Kim
*Attorney, Agent, or Firm*—Janet E. Hasak; Timothy E. Torchia

[57] ABSTRACT

Isolated CHF, isolated DNA encoding CHF, and recombinant or synthetic methods of preparing CHF are disclosed. These CHF molecules are shown to influence hypertrophic activity and neurological activity. Accordingly, these compounds or their antagonists may be used for treatment of heart failure, arrhythmic disorders, inotropic disorders, and neurological disorders.

1 Claim, 5 Drawing Sheets

OTHER PUBLICATIONS

Knowlton et al., "The $\alpha_{1a}$–Adrenergic Receptor Subtype Mediates Biochemical, Molecular, and Morphologic Features of Cultured Myocardial Cell Hypertrophy", *J. Biol. Chem.*, 268(21):15374–15380, (1993).

Knowlton et al., "Co–Regulation of the Atrial Natriuretic Factor and Cardiac Myosin Light Chain–2 Genes During $\alpha$–Adrenergic Stimulation of Neonatal Rat Ventricular Cells", *J. Biol. Chem.*, 266(12):7759–7768, (1991).

Lee et al., "Atrial Natriuretic Factor Gene Expression in Ventricles of Rats with Spontaneous Biventricular Hypertrophy", *J. Clin. Invest.*, 81:431–434, (1988).

Lee et al., "$\alpha_1$–Adrenergic Stimulation of Cardiac Gene Transcription in Neonatal Rat Myocardial Cells", *J. Biol. Chem.*, 263(15):7352–7358, (1988).

Libby, "Long–Term Culture of Contractile Mammalian Heart Cells in a Defined Serum–Free Medium that Limits Non–Muscle Cell Proliferation", *J. Mol. Cell Cardiol.*, 16:803–811, (1984).

Long, "TGF $\beta$ Isoform Expression and Effect in Neonatal Rat Cardiac Myocytes and Non–myocytes in Culture", *Circulation*, Abstracts from the 65th Scientific Sessions, 86:I–837, (1992) (abstract 3332).

Long et al., "Trophic Factors in Cardiac Myoctyes", *J. Hyper.*, 8(Suppl. 7):S219–S224, (1990).

Long et al., "$\beta$–Adrenergic Stimulation of Cardiac Non–myocytes Augments the Growth–promoting Activity of Non–myocyte Conditioned Medium", *J. Mol. Cell. Cardiol.*, 25:915–925, (1993).

Long et al., "A Growth Factor for Cardiac Myocytes is Produced by Cardiac Nonmyocytes", *Cell Reg.*, 2:1081–1095, (1991).

McDonald et al., "Expression and Characterization of Recombinant Human Ciliary Neuroptrophic Factor from *Escherichia coli*", *Biochimica et Biophysica Acta*, 1090:70–80, (1991).

Mir et al., "Isolation of a Negative Inotropic Factor from Blast Cells of Patients with leukaemic Cardiomyophaty", *Circulation*, 55 & 56(Supp III):III–86, (1977) (abstract 324).

Mir, "Evidence for Non–Infiltrative Neoplastic Cardiomyopaty and Presence of Negative Inotropic Factor in Acute Myeloid Leukaemia: A Clinico–Experimental Study", *British Heart J.*, 39(3):355, (1977).

Mukherjee et al., "Myotrophin Induces Early Response Genes and Enhances Cardiac Gene Expression", *Hypertension*, 21(2):142–148, (1993).

Mukherjee et al., "Effect of Myotrophin on Induction of Proto–Oncogenes, ANF and Contractile Element Transcript Levels", *Circulation*(Suppl. I)., 86(4):I–626, (1992) (abstract 2490).

Neben et al., "The Biology of Interleukin 11", *Stem Cells*, 11(Suppl. 2):156–162, (1993).

Patterson, "The Emerging Neuropoietic Cytokine Family: First CDF/LF, CNTF and IL–6; next ONC, MGF, GCSF?", *Curr. Opin. Neurobiol.*, 2:94–97, (1992).

Ramaciotti et al., "Cardiac Endothelial Cells Modulate Contractility of Rat Heart in Response to Oxygen Tension and Coronary Flow", *Circ. Res.*, 72(5):1044–1064, (1993).

Robbins et al., "Mouse Embryonic Stem Cells Express the Cardiac Myosin Heavy Chain Genes During Development *in Vitro*", *J. Biol. Chem.*, 265(20):11905–11909, (1990).

Rockman et al., "Segregation of Atrial–Specific and Inducible Expression of an Atrial Natriuretic Factor Transgene in an *in vivo* Murine Model of Cardiac Hypertrophy", *Proc. Natl. Acad. Sci. USA.*, 88:8277–8281, (1991).

Sadoshima et al., "Autocrine Release of Angiotensin II Mediates Stretch–Induced Hypertrophy of Cardiac Myocytes in Vitro", *Cell*, 75:977–984, (1993).

Sarzani et al., "Regulation of Cardiac Growth Factors and Growth Factor Receptors Gene Expression by Growth Hormone", *Eur. Heart J.*, 13(ABST. SUPPL):326, (1992).

Sen et al., "Myotrophin: Purification of a Novel Peptide from Spontaneously Hypertensive Rat Heart That Influences Myocardial Growth", *J. Biol. Chem.*, 265(27):16635–16643, (1990).

Sen et al., "Basic Science/Circulation: Myocardial Structure and Pathology–Hypertrophy", *Circulation (Suppl. II)*, 80(4):II–616, (1989) (abstract 2445).

Shubeita et al., "Endothelin Induction of Inositol Phospholipid Hydrolysis, Sarcomere Assembly, and Cardiac Gene Expression in Ventricular Myocytes", *J. Biol. Chem.*, 265(33):20555–20562, (1990).

Sil et al., "Myotrophin in Human Cardiomyopathic Heart", *Circ. Res.*, 73(1):98–108, (1993).

Sil et al., "Role of Myotrophic in Pathophysiology of Cardiac Hypertrophy in Spontaneously Hypertensive Rat (SHR)", *Circulation*, 88(4 part 2):I–613, (1993) (abstract 3299).

Sil et al., "Purification of Myotrophin from Human Cardiomyopathic Heart", *FASEB J.* 5(5991):A1244, (1991) (abstract 5069).

Simpson et al., "Myocyte Hypertrophy in Neonatal Rat Heart Cultures and Its Regulation by Serum and by Catecholamines", *Cir. Res.*, 51(6):787–801, (1982).

Simpson et al., "Differentiation of Rat Myoctyes in Single Cell Cultures with and without Proliferating Nonmyocardial Cells", *Circ. Res.*, 50(1):101–116, (1982).

Suzuki et al., "Serum–Free, Chemically Defined Medium is Important to Investigate the Growth, Development and Function of Neonatal Rat Cardiac Myocytes in Culture", *Trends in Animal Cell Culture Technology*, pp. 61–66, Murakami, ed.) (Kodansha Tokyo, 1990).

Takemura et al., "Expression and Distribution of Atrial Natriuretic Peptide in Human Hypertrophic Ventricle of Hypertensive Hearts and Hearts with Hypertrophic Cardiomyopathy", *Circ.*, 83(1):181–190, (1991).

Williams et al., "Cardiovasculr Growth Factors", *The Heart and Cardiovascular System*, pp. 1689–1694, Fozzard et al., ed. (Raven Press, NY, 1986) Chapter 72.

FIG. 1A

```
  1 GGATAAGCCT GGGGCCAGCA TGAGCCAGAG GGAGGGAAGT CTGGAAGACC
    CCTATTCGGA CCCCGGTCGT ACTCGGTCTC CCTCCCTTCA GACCTTCTGG
  1                       M  S  Q  R  E  G  S   L  E  D  H

51 ACCAGACTGA CTCCTCAATC TCATTCCTAC CCCATTTGGA GGCCAAGATC
    TGGTCTGACT GAGGAGTTAG AGTAAGGATG GGGTAAACCT CCGGTTCTAG
 12  Q  T  D   S  S  I    S  F  L  P  H  L  E   A  K  I

101 CGCCAGACAC ACAACCTTGC CCGCCTCCTG ACCAAATATG CAGAACAACT
    GCGGTCTGTG TGTTGGAACG GGCGGAGGAC TGGTTTATAC GTCTTGTTGA
 28  R  Q  T   H  N  L  A  R  L  L   T  K  Y  A  E  Q  L

151 TCTGGAGGAA TACGTGCAGC AACAGGGAGA GCCCTTTGGG CTGCCGGGCT
    AGACCTCCTT ATGCACGTCG TTGTCCCTCT CGGGAAACCC GACGGCCCGA
 45  L  E  E   Y  V  Q  Q  Q  G  E   P  F  G   L  P  G  F

201 TCTCACCACC GCGGCTGCCG CTGGCCGGCC TGAGTGGCCC GGCTCCGAGC
    AGAGTGGTGG CGCCGACGGC GACCGGCCGG ACTCACCGGG CCGAGGCTCG
 62  S  P  P   R  L  P    L  A  G  L  S  G  P   A  P  S

251 CATGCAGGGC TACCGGTGTC CGAGCGGCTG CGGCAGGATG CAGCCGCCCT
    GTACGTCCCG ATGGCCACAG GCTCGCCGAC GCCGTCCTAC GTCGGCGGGA
 78  H  A  G   L  P  V  S  E  R  L   R  Q  D  A  A  A  L

301 GAGTGTGCTG CCCGCGCTGT TGGATGCCGT CCGCCGCCGC CAGGCGGAGC
    CTCACACGAC GGGCGCGACA ACCTACGGCA GGCGGCGGCG GTCCGCCTCG
 95  S  V  L   P  A  L  L  D  A  V   R  R  R   Q  A  E  L

351 TGAACCCGCG CGCCCCGCGC CTGCTGCGGA GCCTGGAGGA CGCAGCCCGC
    ACTTGGGCGC GCGGGGCGCG GACGACGCCT CGGACCTCCT GCGTCGGGCG
112   N  P  R  A  P  R   L  L  R  S   L  E  D  A  A  R

401 CAGGTTCGGG CCCTGGGCGC CGCGGTGGAG ACAGTGCTGG CCGCGCTGGG
    GTCCAAGCCC GGGACCCGCG GCGCCACCTC TGTCACGACC GGCGCGACCC
128  Q  V  R  A  L  G  A  A  V  E    T  V  L  A  A  L  G

451 CGCTGCAGCC CGCGGGCCCG GGCCAGAGCC CGTCACCGTC GCCACCCTCT
    GCGACGTCGG GCGCCCGGGC CCGGTCTCGG GCAGTGGCAG CGGTGGGAGA
145  A  A  A   R  G  P  G  P  E  P   V  T  V   A  T  L  F

501 TCACGGCCAA CAGCACTGCA GGCATCTTCT CAGCCAAGGT GCTGGGGTTC
    AGTGCCGGTT GTCGTGACGT CCGTAGAAGA GTCGGTTCCA CGACCCCAAG
162  T  A  N   S  T  A   G  I  F  S   A  K  V   L  G  F

551 CACGTGTGCG GCCTCTATGG CGAGTGGGTG AGCCGCACAG AGGGCGACCT
    GTGCACACGC CGGAGATACC GCTCACCCAC TCGGCGTGTC TCCCGCTGGA
178  H  V  C   G  L  Y  G  E  W  V   S  R  T   E  G  D  L

601 GGGCCAGCTG GTGCCAGGGG GCGTCGCCTG AGAGTGAATA CTTTTTCTTG
    CCCGGTCGAC CACGGTCCCC CGCAGCGGAC TCTCACTTAT GAAAAAGAAC
195  G  Q  L   V  P  G  G  V  A  O
```

FIG. 1B

```
 651 TAAGCTCGCT CTGTCTCGCC TCTTTGGCTT CAAATTTTCT GTCTCTCCAT
     ATTCGAGCGA GACAGAGCGG AGAAACCGAA GTTTAAAAGA CAGAGAGGTA

701 CTGTGTCCTG TGTGTTCTTG GGCTGTCCCT ATCTTTCTGC ATTTGTGTGG
     GACACAGGAC ACACAAGAAC CCGACAGGGA TAGAAAGACG TAAACACACC

751 TCTCTCTCTT CTGCTCTCCT CTCTGCAGGG AGCTTCTTTT TTCCAACAGT
     AGAGAGAGAA GACGAGAGGA GAGACGTCCC TCGAAGAAAA AAGGTTGTCA

801 TTCTCGTTTT GTCTCTCTCC AGTCTTGAAC ACTTTTGTCT CCGAGAGGTC
     AAGAGCAAAA CAGAGAGAGG TCAGAACTTG TGAAAACAGA GGCTCTCCAG

851 TCTTTTTGTT TCCTTGTCTC TTGGTTCTTT CTTTGCTTGC TTGCTTGCTT
     AGAAAAACAA AGGAACAGAG AACCAAGAAA GAAACGAACG AACGAACGAA

901 GCTTGCTTGT TGTTGAGACA GGGTCTCACC ATATAGCTCT GGATGGCCTG
     CGAACGAACA ACAACTCTGT CCCAGAGTGG TATATCGAGA CCTACCGGAC

951 GAACTTGCTA TGTAGGCCAG GCTGGCCTCC AGCTCATAGA GATCCACTTG
     CTTGAACGAT ACATCCGGTC CGACCGGAGG TCGAGTATCT CTAGGTGAAC

1001 CCTCCGACTC CCAATTTCCC CATCTGTCTC CCTGTGATCC ATATGGGTAT
     GGAGGCTGAG GGTTAAAGGG GTAGACAGAG GGACACTAGG TATACCCATA

1051 GTGTAACCCT TACTTTGTCT CATGGAGGTG ACAATTTTTC TCCCTTCAGT
     CACATTGGGA ATGAAACAGA GTACCTCCAC TGTTAAAAAG AGGGAAGTCA

1101 TTCTTTGTTC TTTACTGACC AGAAAAGTGC CTACTTGTCC CCTGGTGGCA
     AAGAAACAAG AAATGACTGG TCTTTTCACG GATGAACAGG GGACCACCGT

1151 AGGCCATTCA CCTTAGGACC TTCCCACCAG TTCCTTTGTA GGCAAATCCC
     TCCGGTAAGT GGAATCCTGG AAGGGTGGTC AAGGAAACAT CCGTTTAGGG

1201 TCCCCCTTTG AGGTCCTTCC CTTTCATACC GCCCTAGGCT GGTCAATGGA
     AGGGGGAAAC TCCAGGAAGG GAAAGTATGG CGGGATCCGA CCAGTTACCT

1251 GAGAGAAAGG CAGAAAAACA TCTTTAAAGA GTTTTATTTG AGAATAAATT
     CTCTCTTTCC GTCTTTTTGT AGAAATTTCT CAAAATAAAC TCTTATTTAA

1301 AATTTTTGTA AATAAAATGT TTAACAATAA AACTAAACTT TTATGAAAAA
     TTAAAAACAT TTATTTACA  AATTGTTATT TTGATTTGAA AATACTTTTT

1351 AA (polyA)
     TT
```

FIG. 2

```
              10         20         30         40         50
chf.781  MSQREGSLEDHQTDSSISFLPHLEAKIRQTHNLARLLTKYAEQLLEEYVQ
                        **         ***         *  * **
humcntf          MAFTEHSPLTPHRRDLCSRSIWLARKIRSDLTALTESYVK
                      10        20         30        40

60         70         80         90        100
chf.781  QQGEPFGLPGFSPPRLPLAGLSGPAPSHAGLPVSERLRQDAAALSVLPAL
          **        *   * *                 ***    *       *
humcntf  HQGLNKNINLDSADGMPVA----STDQWSELTEAERLQENLQAYRTFHVL
                 50        60         70        80

110        120        130        140
chf.781  LD-AVRRRQAELNPRAPRLLRSLEDAARQVRALGAAVETVLAALGAAARG
           *    *    *                ** *     *        *
humcntf  LARLLEDQQVHFTPTEGDFHQAIHTLLLQVAAFAYQIEELMILLEYKIPR
              90       100        110        120       130

150        160        170        180        190
chf.781  PGPEPVTVATLFTANSTAGIFSAKVLGFHVCGLYGEWVSRTEGDLGQLVP
                         *  *   *  *   *          *  *   **
humcntf  NEADGMPINV-----GDGGLFEKKLWGLKVLQELSQWTVRSIHDL-RFIS
             140        150        160        170       180

200
chf.781  GGVAO humcntf  SHQTGIPARGSHYIANNKKM
                  190        200
```

CARDIAC HYPERTROPHY FACTOR AND USES THEREFOR

FIELD OF THE INVENTION

This application relates to a cardiac hypertrophy factor for modulating cardiac function in the treatment of heart failure and for modulating neural function in the treatment of neurological disorders.

BACKGROUND OF THE INVENTION

Heart failure affects approximately three million Americans, developing in about 400,000 each year. It is currently one of the leading admission diagnoses in the U.S. Recent advances in the management of acute cardiac diseases, including acute myocardial infarction, are resulting in an expanding patient population that will eventually develop chronic heart failure.

Current therapy for heart failure is primarily directed to using angiotensin-converting enzyme (ACE) inhibitors and diuretics. While prolonging survival in the setting of heart failure, ACE inhibitors appear to slow the progression towards end-stage heart failure, and substantial numbers of patients on ACE inhibitors have functional class III heart failure. Moreover, ACE inhibitors consistently appear unable to relieve symptoms in more than 60% of heart failure patients and reduce mortality of heart failure only by approximately 15–20%. Heart transplantation is limited by the availability of donor hearts. Further, with the exception of digoxin, the chronic administration of positive inotropic agents has not resulted in a useful drug without accompanying adverse side effects, such as increased arrhythmogenesis, sudden death, or other deleterious side effects related to survival. These deficiencies in current therapy suggest the need for additional therapeutic approaches.

A wide body of data suggests that pathological hypertrophy of cardiac muscle in the setting of heart failure can be deleterious, characterized by dilation of the ventricular chamber, an increase in wall tension/stress, an increase in the length vs. width of cardiac muscle cells, and an accompanying decrease in cardiac performance and function. Studies have shown that the activation of physiological or compensatory hypertrophy can be beneficial in the setting of heart failure. In fact, the effects of ACE inhibitors have been purported not only to unload the heart, but also to inhibit the pathological hypertrophic response that has been presumed to be linked to the localized renin-angiotensin system within the myocardium.

On a molecular biology level, the heart functions as a syncytium of myocytes and surrounding support cells, called non-myocytes. While non-myocytes are primarily fibroblast/mesenchymal cells, they also include endothelial and smooth muscle cells. Indeed, although myocytes make up most of the adult myocardial mass, they represent only about 30% of the total cell numbers present in heart. Because of their close relationship with cardiac myocytes in vivo, non-myocytes are capable of influencing myocyte growth and/or development. This interaction may be mediated directly through cell-cell contact or indirectly via production of a paracrine factor. Such association in vivo is important since both non-myocyte numbers and the extracellular matrix with which they interact are increased in myocardial hypertrophy and in response to injury and infarction. These changes are associated with abnormal myocardial function.

Cardiac myocytes are unable to divide shortly after birth, Further growth occurs through hypertrophy of the individual cells. Cell culture models of myocyte hypertrophy have been developed to understand better the mechanisms for cardiac myocyte hypertrophy. Simpson et al., *Circ. Res.*, 51: 787–801 (1982); Chien et al., *FASEB J.*, 5: 3037–3046 (1991). Most studies of heart myocytes in culture are designed to minimize contamination by non-myocytes. See, for example, Simpson and Savion, *Cir. Cres.*, 50: 101–116 (1982); Libby, *J. Mol. Cell. Cardiol.*, 16: 803–811 (1984); Iwaki et al., *J. Biol. Chem.*, 265: 13809–13817 (1990).

Shubaita et al., *J. Biol. Chem.*, 265: 20555–20562 (1990) documented the utility of a culture model to identify peptide-derived growth factors such as endothelin-1 that can activate a hypertrophic response. Long et al., *Cell Regulation*, 2: 1081–1095 (1991) investigated the effect of the cardiac non-myocytes on cardiac myocyte growth in culture. Myocyte hypertrophic growth was stimulated in high-density cultures with increased numbers of non-myocytes and in co-cultures with increased numbers of non-myocytes. This effect of non-myocytes on myocyte size could be reproduced by serum-free medium conditioned by non-myocyte cultures. The major myocyte growth-promoting activity in the cultures was heparin binding. The properties of this growth factor were compared to various growth factors known to be present in myocardium, including fibroblast growth factor (FGF), platelet derived growth factor (PDGF), tumor necrosis factor-alpha (TNF-α), and transforming growth factor-betal (TGF-β1). The growth factor of Long et al. was found to be larger than these other known growth factors and to have a different heparin-Sepharose elution profile from that of all these growth factors except PDGF. Further, it was not neutralized by a PDGF-specific antibody. The authors proposed that it defines a paracrine relationship important for cardiac muscle cell growth and development.

Not only is there a need for an improvement in the therapy of heart failure such as congestive heart failure, but there is also a need to offer effective treatment for neurological disorders. Neurotrophic factors such as insulin-like growth factors, nerve growth factor, brain-derived neurotrophic factor, neurotrophin-3, -4, and -5, and ciliary neurotrophic factor have been proposed as potential means for enhancing neuronal survival, for example, as a treatment for neurodegenerative diseases such as amyotrophic lateral sclerosis, Alzheimer's disease, stroke, epilepsy, Huntington's disease, Parkinson's disease, and peripheral neuropathy. It would be desirable to provide an additional therapy for this purpose.

Accordingly, it is an object of the present invention to provide an improved therapy for the prevention and/or treatment of heart failure such as congestive heart failure, particularly the promotion of physiological forms of hypertrophy or inhibition of pathological forms of hypertrophy, and for the prevention and/or treatment of neurological disorders such as peripheral neuropathy.

It is another object to identify a novel group of cardiac hypertrophy factor polypeptides and antagonists thereto for use in such therapies.

It is yet another object to provide nucleic acid encoding such polypeptides and to use this nucleic acid to produce the polypeptides in recombinant cell culture.

It is a still further object to provide derivatives and modified forms of such polypeptides, including amino acid sequence variants and covalent derivatives thereof.

It is an additional object to prepare immunogens for raising antibodies against such polypeptides, as well as to obtain antibodies capable of binding them.

It is still another object to provide a novel hypertrophy assay that can be used, for example, in expression cloning and purification of such polypeptides, in evaluation of clones isolated from the expression cloning, and in identification of antagonists to such polypeptides.

These and other objects of the invention will be apparent to the ordinarily skilled artisan upon consideration of the specification as a whole.

SUMMARY OF THE INVENTION

An in vitro neonatal rat heart hypertrophy assay has been developed that allows for expression cloning and protein purification of the cardiac hypertrophy factor (CHF) disclosed herein. The assay capacity of 1000 single samples a week coupled with the small sample size requirement of 100 µL or less has enabled expression cloning and protein purification that would have been impossible using the currently published methods. Hence, in one embodiment, the invention provides a method for assaying a test sample for hypertrophic activity comprising:

(a) plating 96-well plates with a suspension of myocytes at a cell density of about $7.5 \times 10^4$ cells per mL in Dulbecco's modified Eagle's medium (D-MEM)/F-12 medium comprising insulin, transferrin, and aprotinin;

(b) culturing the cells;

(c) adding the test sample (such as one suspected of containing a CHF) to the cultured cells;

(d) culturing the cells with the test sample; and (e) determining if the test sample has hypertrophic activity.

Besides the assay, the invention provides isolated CHF polypeptide, excluding rat CHF polypeptide. This CHF polypeptide is preferably substantially homogeneous, may be glycosylated or unglycosylated, and may be selected from the group consisting of the native sequence polypeptide, a fragment polypeptide, a variant polypeptide, and a chimeric polypeptide. Additionally, the CHF polypeptide may be selected from the group consisting of the polypeptide that is isolated from a mammal, the polypeptide that is made by recombinant means, and the polypeptide that is made by synthetic means. Further, this CHF polypeptide may be selected from the group consisting of the polypeptide that is human and the polypeptide that is non-immunogenic in a human.

In another aspect, the isolated CHF polypeptide shares at least 80% amino acid sequence identity with the translated CHF sequence shown in FIG. 1.

In a further aspect, the invention provides an isolated polypeptide encoded by a nucleic acid having a sequence that hybridizes under moderately stringent conditions to the nucleic acid sequence provided in FIG. 1. Preferably, this polypeptide is biologically active.

In another aspect, the invention provides a chimera comprising CHF fused to a heterologous polypeptide.

In a still further aspect, the invention provides a composition comprising biologically active CHF and a pharmaceutically acceptable carrier or comprising biologically active CHF fused to an immunogenic polypeptide.

In yet another aspect, the invention provides an isolated antibody that is capable of binding CHF and a method for detecting CHF in vitro or in vivo comprising contacting the antibody with a sample or cell suspected of containing CHF and detecting if binding has occurred, as with an ELISA.

In still another aspect, the invention provides a method for purifying CHF comprising passing a mixture of CHF over a column to which is bound the antibodies and recovering the fraction containing CHF.

In other aspects, the invention comprises an isolated nucleic acid molecule encoding CHF, a vector comprising the nucleic acid molecule, preferably an expression vector comprising the nucleic acid molecule operably linked to control sequences recognized by a host cell transformed with the vector, a host cell comprising the vector, including mammalian and bacterial host cells, and a method of using a nucleic acid molecule encoding CHF to effect the production of CHF, comprising culturing a host cell comprising the vector. Preferably the host cell is transfected to express CHF nucleic acid and the CHF is recovered from the host cell culture, and if secreted, recovered from the culture medium.

In additional aspects, the invention provides an isolated nucleic acid molecule comprising the open reading frame nucleic acid sequence shown in FIG. 1. The invention also provides an isolated nucleic acid molecule excluding rat CHF selected from the group consisting of:

(a) a cDNA clone comprising the nucleotide sequence of the coding region of the CHF gene shown in FIG. 1;

(b) a DNA sequence capable of hybridizing under stringent conditions to a clone of (a); and (c) a genetic variant of any of the DNA sequences of (a) and (b) which encodes a polypeptide possessing a biological property of a native CHF polypeptide.

The invention also provides an isolated DNA molecule having a sequence capable of hybridizing to the DNA sequence provided in FIG. 1 under moderately stringent conditions, wherein the DNA molecule encodes a biologically active CHF polypeptide, excluding rat CHF.

In yet another aspect, a method is provided of determining the presence of a CHF nucleic acid molecule in a test sample comprising contacting the CHF nucleic acid molecule with the test sample and determining whether hybridization has occurred, or comprising hybridizing the CHF nucleic acid molecule to a test sample nucleic acid and determining the presence of CHF nucleic acid.

In still another aspect, the invention provides a method of amplifying a nucleic acid test sample comprising priming a nucleic acid polymerase chain reaction in the test sample with the CHF nucleic acid molecule.

In a still further aspect, the invention provides a CHF antagonist and a method of identifying such antagonist comprising using cell supernatants as the test sample in the hypertrophy assay as described above and screening for molecules that antagonize the hypertrophic activity of a CHF demonstrated in such assay.

In a still further aspect, the invention provides a method for treating a mammal having or at risk for heart failure, an inotropic disorder, or an arrhythmic disorder comprising administering to a mammal in need of such treatment a therapeutically effective amount of a pharmaceutical composition comprising the CHF or a CHF antagonist in a pharmaceutically acceptable carrier.

The invention also provides a method for treating a mammal having or at risk for a neurological disorder comprising administering to a mammal in need of such treatment a therapeutically effective amount of a pharmaceutical composition comprising the CHF in a pharmaceutically acceptable carrier.

In additional embodiments, the invention supplies a method of identifying a receptor for CHF comprising using labeled CHF, preferably radiolabeled CHF, in a cellular receptor assay, allowing the CHF to bind to cells, or using the labeled CHF to pan for cells that contain the receptor.

BRIEF DESCRIPTION OF THE DRAWINGS

FIGS. 1A and 1B depict the nucleotide sequence (sense and anti-sense strands) (SEQ ID NOS: 1 and 2) and deduced amino acid sequence (SEQ ID NO: 3) of a mouse CHF DNA clone. The underlined complementary nucleotides at position 27 show the start of another mouse CHF clone used to obtain the full-length clone.

FIG. 2 aligns the translated amino acid sequence of the mouse CHF clone (chf.781) (SEQ ID NO: 3) with the amino acid sequence of human ciliary neurotrophic factor (humcntf) (SEQ ID NO: 4) to show the extent of sequence identity.

DETAILED DESCRIPTION OF THE PREFERRED EMBODIMENTS

I. Definitions

Figure 3:
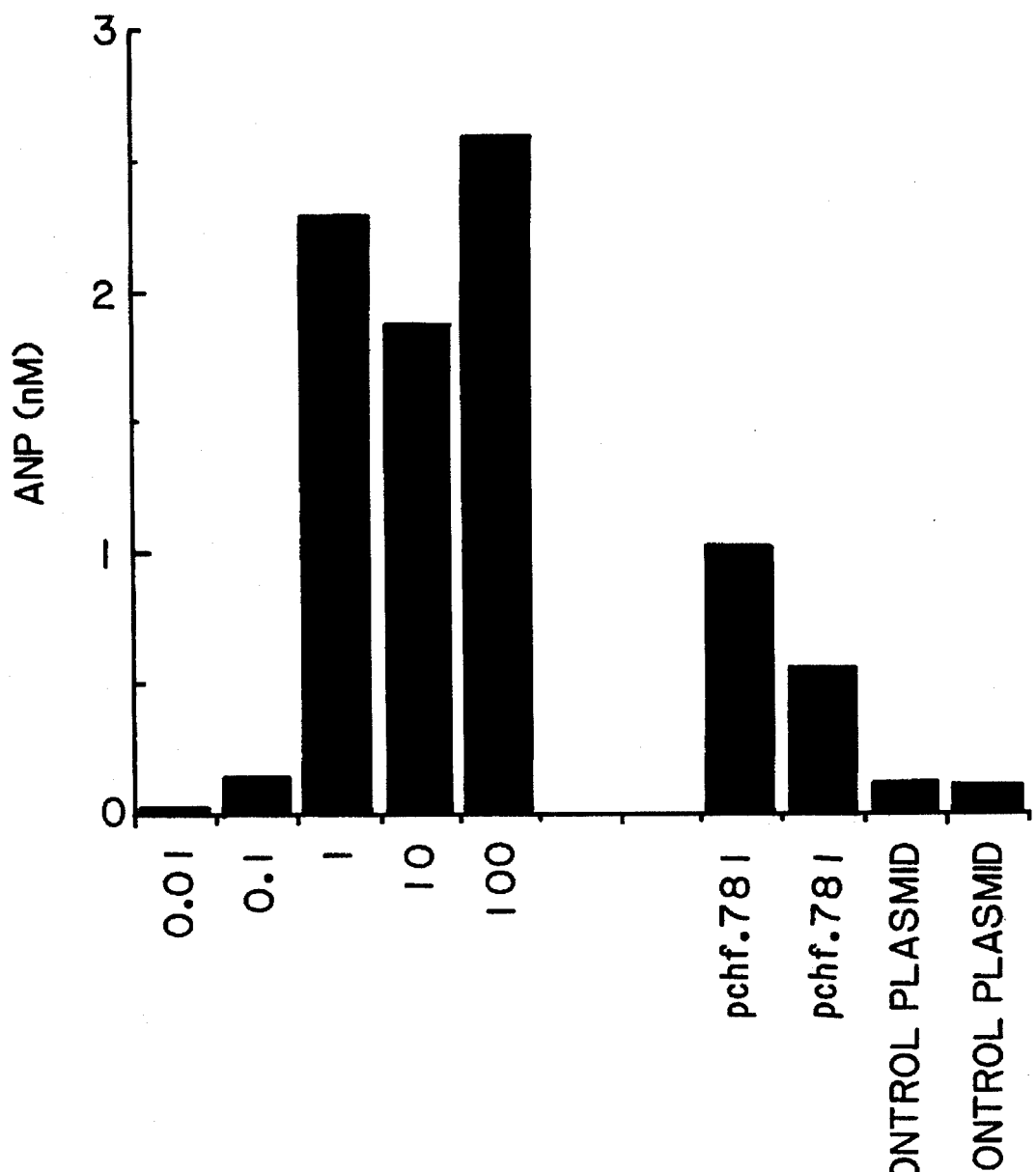
FIG. 3 shows a graph of atrial natriuretic peptide (ANP) release for phenylephrine (standard curve) and transfections into 293 cells in a neonatal cardiac hypertrophy assay.

In general, the following words or phrases have the indicated definition when used in the description, examples, and claims:

"CHF" (or "cardiac hypertrophy factor") is defined herein to be any polypeptide sequence that possesses a biological property of a naturally occurring polypeptide comprising the polypeptide sequence of FIG. 1 or a human equivalent thereof. It does not include the rat homolog of CHF, i.e., CHF from the rat species. This definition encompasses not only the polypeptide isolated from a CHF source such as murine embryoid bodies described herein or from another source, such as another animal species except rat, including humans, but also the polypeptide prepared by recombinant or synthetic methods. It also includes variant forms including functional derivatives, fragments, alleles, isoforms and analogues thereof.

A "CHF fragment" is a portion of a naturally occurring mature full-length CHF sequence having one or more amino acid residues or carbohydrate units deleted. The deleted amino acid residue(s) may occur anywhere in the polypeptide, including at either the N-terminal or C-terminal end or internally. The fragment will share at least one biological property in common with CHF. CHF fragments typically will have a consecutive sequence of at least 10, 15, 20, 25, 30, or 40 amino acid residues that are identical to the sequences of the CHF isolated from a mammal including the CHF isolated from murine embryoid bodies or the human CHF.

"CHF variants" or "CHF sequence variants" as defined herein mean biologically active CHFs as defined below having less than 100% sequence identity with the CHF isolated from recombinant cell culture or from murine embryoid bodies having the deduced sequence described in FIG. 1, or with the human equivalent. Ordinarily, a biologically active CHF variant will have an amino acid sequence having at least about 70% amino acid sequence identity with the CHF isolated from murine embryoid bodies or the mature human CHF or fragments thereof (see FIG. 1), preferably at least about 75%, more preferably at least about 80%, still more preferably at least about 85%, even more preferably at least about 90%, and most preferably at least about 95%.

A "chimeric CHF" is a polypeptide comprising full-length CHF or one or more fragments thereof fused or bonded to a second protein or one or more fragments thereof. The chimera will share at least one biological property in common with CHF. The second protein will typically be a cytokine, growth factor, or hormone such as growth hormone, IGF-I, or a neurotrophic factor such as CNTF, nerve growth factor (NGF), brain-derived neurotrophic factor (BDNF), neurotrophin-3 (NT-3), neurotrophin-4 (NT-4), neurotrophin-5 (NT-5), etc.

"Isolated CHF", "highly purified CHF" and "substantially homogeneous CHF" are used interchangeably and mean a CHF that has been purified from a CHF source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Biological property" when used in conjunction with either "CHF" or "isolated CHF" means having myocardiotrophic, inotropic, anti-arrhythmic, or neurotrophic activity or having an in vivo effector or antigenic function or activity that is directly or indirectly caused or performed by a CHF (whether in its native or denatured conformation) or a fragment thereof. Effector functions include receptor binding and any carrier binding activity, agonism or antagonism of CHF, especially transduction of a proliferative signal including replication, DNA regulatory function, modulation of the biological activity of other growth factors, receptor activation, deactivation, up- or down-regulation, cell growth or differentiation, and the like. However, effector functions do not include possession of an epitope or antigenic site that is capable of cross-reacting with antibodies raised against native CHF.

An "antigenic function" means possession of an epitope or antigenic site that is capable of cross-reacting with antibodies raised against the native CHF of FIG. 1 or another mammalian, including human, homolog thereof. The principal antigenic function of a CHF polypeptide is that it binds with an affinity of at least about $10^6$ L/mole to an antibody raised against CHF isolated from mouse embryoid bodies or a human homolog thereof. Ordinarily, the polypeptide binds with an affinity of at least about $10^7$ L/mole. Most preferably, the antigenically active CHF polypeptide is a polypeptide that binds to an antibody raised against CHF having one of the above-described effector functions. The antibodies used to define "biologically activity" are rabbit polyclonal antibodies raised by formulating the CHF isolated from recombinant cell culture or embryoid bodies in Freund's complete adjuvant, subcutaneously injecting the formulation, and boosting the immune response by intraperitoneal injection of the formulation until the titer of the anti-CHF antibody plateaus.

"Biologically active" when used in conjunction with either "CHF" or "isolated CHF" mean a CHF polypeptide that exhibits hypertrophic, inotropic, anti-arrhythmic, or neurotrophic activity or shares an effector function of CHF isolated from murine embryoid bodies or produced in recombinant cell culture described herein, and that may (but need not) in addition possess an antigenic function. One principal effector function of CHF or CHF polypeptide herein is influencing cardiac growth or hypertrophy activity, as measured, e.g., by atrial natriuretic peptide (ANP) release or by the myocyte hypertrophy assay described herein using a specific plating medium and plating density, and preferably using crystal violet stain for readout. The desired function of a CHF (or CHF antagonist) is to increase physiological (beneficial) forms of hypertrophy and decrease pathological hypertrophy. In addition, the CHF herein is expected to display anti-arrhythmic function by promoting a more normal electrophysiological phenotype. Another principal effector function of CHF or CHF polypeptide herein is stimulating the proliferation of chick ciliary ganglion neurons in an assay for CNTF activity.

Antigenically active CHF is defined as a polypeptide that possesses an antigenic function of CHF and that may (but need not) in addition possess an effector function.

In preferred embodiments, antigenically active CHF is a polypeptide that binds with an affinity of at least about $10^6$ L/mole to an antibody capable of binding CHF. Ordinarily, the polypeptide binds with an affinity of at least about $10^7$ L/mole. Isolated antibody capable of binding CHF is an antibody that is identified and separated from a component of the natural environment in which it may be present. Most preferably, the antigenically active CHF is a polypeptide that binds to an antibody capable of binding CHF in its native conformation. CHF in its native conformation is CHF as found in nature that has not been denatured by chaotropic agents, heat, or other treatment that substantially modifies the three-dimensional structure of CHF as determined, for example, by migration on non-reducing, non-denaturing sizing gels. Antibody used in this determination is rabbit polyclonal antibody raised by formulating native CHF from a non-rabbit species in Freund's complete adjuvant, subcutaneously injecting the formulation, and boosting the immune response by intraperitoneal injection of the formulation until the titer of anti-CHF antibody plateaus.

"Percent amino acid sequence identity" with respect to the CHF sequence is defined herein as the percentage of amino acid residues in the candidate sequence that are identical with the residues in the CHF sequence isolated from murine embryoid bodies having the deduced amino acid sequence described in FIG. 1, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the CHF sequence shall be construed as affecting sequence identity or homology. Thus, exemplary biologically active CHF polypeptides considered to have identical sequences include prepro-CHF, pro-CHF, and mature CHF.

"CHF microsequencing" may be accomplished by any appropriate standard procedure provided the procedure is sensitive enough. In one such method, highly purified polypeptide obtained from SDS gels or from a final HPLC step is sequenced directly by automated Edman (phenyl isothiocyanate) degradation using a model 470A Applied Biosystems gas phase sequencer equipped with a 120A phenylthiohydantoin (PTH) amino acid analyzer. Additionally, CHF fragments prepared by chemical (e.g., CNBr, hydroxylamine, or 2-nitro-5-thiocyanobenzoate) or enzymatic (e.g., trypsin, clostripain, or staphylococcal protease) digestion followed by fragment purification (e.g., HPLC) may be similarly sequenced. PTH amino acids are analyzed using the ChromPerfect™ data system (Justice Innovations, Palo Alto, Calif.). Sequence interpretation is performed on a VAX 11/785 Digital Equipment Co. computer as described by Henzel et al., *J. Chromatography*, 404:41–52 (1987). Optionally, aliquots of HPLC fractions may be electrophoresed on 5–20% SDS-PAGE, electrotransferred to a PVDF membrane (ProBlott, AIB, Foster City, Calif.) and stained with Coomassie Brilliant Blue. Matsurdiara, *J. Biol. Chem.*, 262: 10035–10038 (1987). A specific protein identified by the stain is excised from the blot and N-terminal sequencing is carried out with the gas phase sequenator described above. For internal protein sequences, HPLC fractions are dried under vacuum (SpeedVac), resuspended in appropriate buffers, and digested with cyanogen bromide, the Lys-specific enzyme Lys-C (Wako Chemicals, Richmond, Va.), or Asp-N (Boehringer Mannheim, Indianapolis, Ind.). After digestion, the resultant peptides are sequenced as a mixture or after HPLC resolution on a C4 column developed with a propanol gradient in 0.1% trifluoroacetic acid (TFA) prior to gas phase sequencing.

"Isolated CHF nucleic acid" is RNA or DNA containing greater than 16 and preferably 20 or more sequential nucleotide bases that encode biologically active CHF or a fragment thereof, is complementary to the RNA or DNA, or hybridizes to the RNA or DNA and remains stably bound under moderate to stringent conditions. This RNA or DNA is free from at least one contaminating source nucleic acid with which it is normally associated in the natural source and preferably substantially free of any other mammalian RNA or DNA. The phrase "free from at least one contaminating source nucleic acid with which it is normally associated" includes the case where the nucleic acid is present in the source or natural cell but is in a different chromosomal location or is otherwise flanked by nucleic acid sequences not normally found in the source cell. An example of isolated CHF nucleic acid is RNA or DNA that encodes a biologically active CHF sharing at least 75%, more preferably at least 80%, still more preferably at least 85%, even more preferably 90%, and most preferably 95% sequence identity with the murine CHF.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

"Exogenous" when referring to an element means a nucleic acid sequence that is foreign to the cell, or homologous to the cell but in a position within the host cell nucleic acid in which the element is ordinarily not found.

"Cell," "cell line," and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Plasmids" are autonomously replicating circular DNA molecules possessing independent origins of replication and are designated herein by a lower case "p" preceded and/or followed by capital letters and/or numbers. The starting plasmids herein either are commercially available, are publicly available on an unrestricted basis, or can be constructed from such available plasmids in accordance with published procedures. In addition, other equivalent plasmids are known in the art and will be apparent to the ordinary artisan.

"Restriction enzyme digestion" when referring to DNA means catalytic cleavage of internal phosphodiester bonds of DNA with an enzyme that acts only at certain locations or sites in the DNA sequence. Such enzymes are called "restriction endonucleases." Each restriction endonuclease recognizes a specific DNA sequence called a "restriction site" that exhibits two-fold symmetry. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1–2 units of enzyme in about 20 µL of buffer solution. Appropriate buffers and substrate amounts for particular restriction enzymes are specified by the manufacturer. Incubation for about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction-cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al., *Molecular Cloning: A Laboratory Manual* (New York: Cold Spring Harbor Laboratory Press, 1989).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9: 6103–6114 (1981) and Goeddel et al., *Nucleic Acids Res.*, 8: 4057 (1980).

"Southern analysis" or "Southern blotting" is a method by which the presence of DNA sequences in a restriction endonuclease digest of DNA or a DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

"Preparation" of DNA from cells means isolating the plasmid DNA from a culture of the host cells. Commonly used methods for DNA preparation are the large- and small-scale plasmid preparations described in sections 1.25–1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods such as phosphotriester, phosphite, or phosphoramidite chemistry, using solid-phase techniques such as described in EP 266,032 published 4 May 1988, or via deoxynucleoside H-phosphonate intermediates as described by Froehler et al., *Nucl. Acids Res.*, 14: 5399–5407 (1986). Further methods include the polymerase chain reaction defined below and other autoprimer methods and oligonucleotide syntheses on solid supports. All of these methods are described in Engels et al., *Agnew. Chem. Int.*

*Ed. Engl.*, 28: 716–734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides are then purified on polyacrylamide gels.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, (Stockton Press, N.Y., 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Stringent conditions" are those that (1) employ low ionic strength and high temperature for washing, for example, 0,015M NACl/0.0015M sodium citrate/0.1% NaDodSO$_4$ (SDS) at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC and 0.1% SDS.

"Moderately stringent conditions" are described in Sambrook et al., supra, and include the use of a washing solution and hybridization conditions (e.g., temperature, ionic strength, and % SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37°–50° C. The skilled artisan will recognize how to adjust the temperature, ionic strength, etc., as necessary to accommodate factors such as probe length and the like.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., *J. Mol. Biol.*, 186: 651–663 [1985]; Novotny and Haber, *Proc. Natl. Acad. Sci. USA*, 82: 4592–4596 [1985]).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, National Institute of Health, Bethesda, Md. [1987]). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$–$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (k) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG-1, IgG-2, IgG-3, IgG-4, IgA-1, and IgA-2. The heavy-chain constant domains that correspond to the different classes of immunoglobulins are called α, delta, epsilon, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256: 495 (1975), or may be made by recombinant DNA methods (see, e.g., U.S. Pat. No. 4,816,567 [Cabilly et al.]).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. USA*, 81: 6851–6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature*, 321: 522–525 (1986); Reichmann et al., *Nature*, 332: 323–329 (1988); and Presta, *Curr. Op. Struct. Biol.*, 2: 593–596 (1992).

"Non-immunogenic in a human" means that upon contacting the polypeptide in a pharmaceutically acceptable carrier and in a therapeutically effective amount with the appropriate tissue of a human, no state of sensitivity or resistance to the polypeptide is demonstratable upon the second administration of the polypeptide after an appropriate latent period (e.g., 8 to 14 days).

"Neurological disorder" refers to a disorder of neurons, including both peripheral neurons and neurons from the central nervous system. Examples of such disorders include all neurodegenerative diseases, such as peripheral neuropathies (motor and sensory), amyotrophic lateral sclerosis (ALS), Alzheimer's disease, Parkinson's disease, stroke, Huntington's disease, epilepsy, and ophthalmologic diseases such as those involving the retina, e.g., diabetic retinopathy, retinal dystrophy, and retinal degeneration caused by infantile malignant osteopetrosis, ceroidlipofuscosis, or cholestasis, or caused by photodegeneration, trauma, axotomy, neurotoxic-excitatory degeneration, or ischemic neuronal degeneration.

"Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine.

"Heart failure" refers to an abnormality of cardiac function where the heart does not pump blood at the rate needed for the requirements of metabolizing tissues. Heart failure includes a wide range of disease states such as congestive heart failure, myocardial infarction, and tachyarrhythmia.

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

II. Modes for Practicing the Invention

1. CHF Polypeptides

Preferred polypeptides of this invention are substantially homogeneous polypeptide(s), referred to as CHF, and having the biological properties of having myocyte hypertrophy and of stimulating the development of chick ciliary neurons in a CNTF assay. More preferred CHFs are isolated mammalian protein(s) having hypertrophic, anti-arrhythmic, inotropic, and neurological activity. Most preferred polypeptides of this invention are mouse and human CHFs including fragments thereof having hypertrophic, anti-arrhythmic, inotropic, and neurological activity. Optionally these murine and human CHFs lack glycosylation.

Optional preferred polypeptides of this invention are biologically active CHF variant(s) with an amino acid sequence having at least 70% amino acid sequence identity with the murine CHF of FIG. 1, preferably at least 75%, more preferably at least 80%, still more preferably at least 85%, even more preferably at least 90%, and most preferably at least 95% (i.e., 70–100%, 75–100%, 80–100%, 85–100%, 90–100%, and 95–100% sequence identity, respectively).

The CHF cloned from murine embryoid bodies has the following characteristics:

(1) It has a molecular weight of about 21–23 kD as measured by reducing SDS-PAGE;

(2) It shows positive activity in the CNTF chick ciliary neuron assay and in the myocyte hypertrophy and ANP-release hypertrophy assays.

More preferred CHF polypeptides are those encoded by genomic DNA or cDNA and having an amino acid sequence described in FIG. 1 or the amino acid sequence of human CHF.

Other preferred naturally occurring biologically active CHF polypeptides of this invention include prepro-CHF, pro-CHF, pre-CHF, mature CHF, CHF fragments, and glycosylation variants thereof.

Still other preferred polypeptides of this invention include CHF sequence variants and chimeras. Ordinarily, preferred CHF sequence variants and chimeras are biologically active CHF variants that have an amino acid sequence having at least 70% amino acid sequence identity with the human or murine CHF, preferably at least 75%, more preferably at least 80%, still more preferably at least 85%, even more preferably at least 90%, and most preferably at least 95%. An exemplary preferred CHF variant is a C-terminal domain CHF variant in which one or more of the basic or dibasic amino acid residue(s) (e.g., R or K) is substituted with a non-basic amino acid residue(s) (e.g., hydrophobic, neutral, acidic, aromatic, gly, pro and the like). An exemplary preferred chimera is a fusion between CHF or a CHF fragment thereof (defined below) a different growth factor, hormone, or cytokine, including CNTF, or fragment thereof.

Another exemplary preferred CHF is a "domain chimera" that consists of the N-terminal residues substituted with one or more, but not all, of the human CNTF residues approximately aligned as shown in FIG. 2. In this embodiment, the CHF chimera would have individual or blocks of residues from the human CNTF sequence added or substituted into the CHF sequence at positions corresponding to the alignment shown in FIG. 2. For example, one or more of those segments of CNTF that are not homologous could be substituted into the corresponding segments of CHF. It is contemplated that this "CHF-CNTF domain chimera" will have mixed hypertrophic/anti-arrhythmic/inotropic/neurotrophic biological activity.

Other preferred polypeptides of this invention include CHF fragments having a consecutive sequence of at least 10, 15, 20, 25, 30, or 40 amino acid residues, preferably about 10–150 residues, that is identical to the sequence of the CHF isolated from murine embryoid bodies or to that of the corresponding human CHF. Other preferred CHF fragments include those produced as a result of chemical or enzymatic hydrolysis or digestion of the purified CHF.

Another aspect of the invention is a method for purifying CHF molecules comprising contacting a CHF source containing the CHF molecules to be purified with an immobilized receptor or antibody polypeptide, under conditions whereby the CHF molecules to be purified are selectively adsorbed onto the immobilized receptor or antibody polypeptide, washing the immobilized support to remove non-adsorbed material, and eluting the molecules to be purified from the immobilized receptor or antibody polypeptide to which they are adsorbed with an elution buffer. The source containing the CHF may be a cell suspension of embryoid bodies.

Alternatively, the source containing the CHF is recombinant cell culture where the concentration of CHF in either the culture medium or in cell lysates is generally higher than in plasma or other natural sources. In this case the above-described immunoaffinity method, while still useful, is usually not necessary and more traditional protein purification methods known in the art may be applied. Briefly, the preferred purification method to provide substantially homogeneous CHF comprises: removing particulate debris by, for example, centrifugation or ultrafiltration; optionally concentrating the protein pool with a commercially available protein concentration filter; and thereafter purifying the CHF from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cationexchange resin such as DEAE; chromatofocusing; SDS-PAGE; ammonium sulfate precipitation; Toyopearl and MONO-Q or MONO-S chromatography; gel filtration using, for example, Sephadex G-75; chromatography on columns that bind the CHF, and protein A Sepharose columns to remove contaminants such as IgG. One preferred purification scheme for both native and recombinant CHF uses a Butyl Toyopearl column followed by a MONO-Q column and a reverse-phase C4 column as described further below.

In another preferred embodiment, this invention provides an isolated antibody capable of binding to the CHF. A preferred isolated anti-CHF antibody is monoclonal (Kohler and Milstein, *Nature,* 256: 495–497 [1975]; Campbell, *Laboratory Techniques in Biochemistry and Molecular Biology,* Burdon et al., Eds, Volume 13, Elsevier Science Publishers, Amsterdam [1985]; and Huse et al., *Science,* 246: 1275–1281 [1989]). Preferred isolated anti-CHF antibody is one that binds to CHF with an affinity of at least about $10^6$ L/mole. More preferably the antibody binds with an affinity of at least about $10^7$ L/mole. Most preferably, the antibody is raised against a CHF having one of the above-described effector functions.

The isolated antibody capable of binding to the CHF may optionally be fused to a second polypeptide and the antibody or fusion thereof may be used to isolate and purify CHF from a source as described above for immobilized CHF polypeptide. In a further preferred aspect of this embodiment, the invention provides a method for detecting the CHF in vitro or in vivo comprising contacting the antibody with a sample, especially a serum sample, suspected of containing the CHF and detecting if binding has occurred.

The invention also provides an isolated nucleic acid molecule encoding the CHF or fragments thereof, which nucleic acid molecule may be labeled or unlabeled with a detectable moiety, and a nucleic acid molecule having a sequence that is complementary to, or hybridizes under stringent or moderately stringent conditions with, a nucleic acid molecule having a sequence encoding a CHF. A preferred CHF nucleic acid is RNA or DNA that encodes a biologically active CHF sharing at least 75%, more preferably at least 80%, still more preferably at least 85%, even more preferably 90%, and most preferably 95%, sequence identity with the murine or human CHF.

More preferred isolated nucleic acid molecules are DNA sequences encoding biologically active CHF, selected from: (a) DNA based on the coding region of a mammalian CHF gene (e.g., DNA comprising the nucleotide sequence provided in FIG. 1, or fragments thereof); (b) DNA capable of hybridizing to a DNA of (a) under at least moderately stringent conditions; and (c) DNA that is degenerate to a DNA defined in (a) or (b) which results from degeneracy of the genetic code. It is contemplated that the novel CHFs described herein may be members of a family of ligands having suitable sequence identity that their DNA may hybridize with the DNA of FIG. 1 (or fragments thereof) under low to moderate stringency conditions. Thus, a further aspect of this invention includes DNA that hybridizes under low to moderate stringency conditions with DNA encoding the CHF polypeptides.

Preferably, the nucleic acid molecule is cDNA encoding the CHF and further comprises a replicable vector in which the cDNA is operably linked to control sequences recognized by a host transformed with the vector. This aspect further includes host cells transformed with the vector and a method of using the cDNA to effect production of CHF, comprising expressing the cDNA encoding the CHF in a culture of the transformed host cells and recovering the CHF from the host cell culture. The CHF prepared in this manner is preferably substantially homogeneous murine or human CHF.

The invention further includes a preferred method for treating a mammal having heart failure, or an arrhythmic, inotropic, or neurological disorder, comprising administering a therapeutically effective amount of a CHF to the mammal. Optionally, the CHF is administered in combination with an ACE inhibitor, such as Captopril™ ACE inhibitor, in the case of congestive heart failure, or with another myocardiotrophic, anti-arrhythmic, or inotropic factor in the case of other types of heart failure or cardiac disorder, or with a neurotrophic molecule such as, e.g., IGF-I, CNTF, NGF, NT-3, BDNF, NT-4, NT-5, etc. in the case of a neurological disorder.

2. Preparation of Natural-Sequence CHF and Variants

Most of the discussion below pertains to production of CHF by culturing cells transformed with a vector containing CHF nucleic acid and recovering the polypeptide from the cell culture. It is further envisioned that the CHF of this invention may be produced by homologous recombination, as provided for in WO 91/06667 published 16 May 1991. Briefly, this method involves transforming primary mammalian cells containing endogenous CHF gene (e.g., human cells if the desired CHF is human) with a construct (i.e., vector) comprising an amplifiable gene (such as dihydrofolate reductase [DHFR] or others discussed below) and at least one flanking region of a length of at least about 150 bp that is homologous with a DNA sequence at the locus of the coding region of the CHF gene to provide amplification of the CHF gene. The amplifiable gene must be at a site that does not interfere with expression of the CHF gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing CHF are grown so as to express the gene and produce the protein.

A. Isolation of DNA Encoding CHF

The DNA encoding CHF may be obtained from any cDNA library prepared from tissue believed to possess the CHF mRNA and to express it at a detectable level. The mRNA is prepared from seven-day differentiated embryoid bodies. The CHF gene may also be obtained from a genomic library or by in vitro oligonucleotide synthesis as defined above assuming the complete nucleotide or amino acid sequence is known.

Libraries are screened with probes designed to identify the gene of interest or the protein encoded by it. For cDNA expression libraries, suitable probes include monoclonal or polyclonal antibodies that recognize and specifically bind to the CHF; oligonucleotides of about 20–80 bases in length that encode known or suspected portions of the CHF cDNA from the same or different species; and/or complementary or homologous cDNAs or fragments thereof that encode the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in chapters 10–12 of Sambrook et al. supra.

An alternative means to isolate the gene encoding CHF is to use PCR methodology as described in section 14 of Sambrook et al., supra. This method requires the use of oligonucleotide probes that will hybridize to the CHF. Strategies for selection of oligonucleotides are described below.

A preferred method of practicing this invention is to use carefully selected oligonucleotide sequences to screen cDNA libraries from various tissues, preferably mammalian differentiated embryoid bodies and placental, cardiac, and brain cell lines. More preferably, human embryoid, placental, cardiac, and brain cDNA libraries are screened with the oligonucleotide probes.

The oligonucleotide sequences selected as probes should be of sufficient length and sufficiently unambiguous that false positives are minimized. The actual nucleotide sequence(s) is usually based on conserved or highly homologous nucleotide sequences. The oligonucleotides may be degenerate at one or more positions. The use of degenerate oligonucleotides may be of particular importance where a library is screened from a species in which preferential codon usage is not known.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the CHF nucleic acid that encodes a full-length polypeptide. In some preferred embodiments, the nucleic acid sequence includes the native CHF signal sequence. Nucleic acid having all the protein coding sequence is obtained by screening selected cDNA or genomic libraries using the deduced amino acid sequence disclosed herein for the first time, and, if necessary, using conventional primer extension procedures as described in section 7.79 of Sambrook et al., supra, to detect precursors and processing intermediates of mRNA that may not have been reverse-transcribed into cDNA.

B. Amino Acid Sequence Variants of Native CHF

Amino acid sequence variants of CHF are prepared by introducing appropriate nucleotide changes into the CHF DNA, or by in vitro synthesis of the desired CHF polypeptide. Such variants include, for example, deletions from, or insertions or substitutions of, residues within the amino acid sequence shown for murine CHF in FIG. 1. Any combination of deletion, insertion, and substitution is made to arrive at the final construct, provided that the final construct possesses the desired characteristics. Excluded from the scope of this invention are CHF variants or polypeptide sequences that are the rat homolog of CHF. The amino acid changes also may alter post-translational processes of the CHF, such as changing the number or position of glycosylation sites.

For the design of amino acid sequence variants of CHF, the location of the mutation site and the nature of the mutation will depend on the CHF characteristic(s) to be modified. For example, candidate CHF antagonists or super agonists will be initially selected by locating sites that are identical or highly conserved among CHF and other ligands binding to members of the growth hormone (GH)/cytokine receptor family, especially CNTF and leukemia inhibitory factor (LIF). The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the CHF polypeptide that are preferred locations for mutagenesis is called "alanine scanning mutagenesis," as described by Cunningham and Wells, Science, 244: 1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the CHF variants produced are screened for the optimal combination of desired activity.

There are two principal variables in the construction of amino acid sequence variants: the location of the mutation site and the nature of the mutation. These are variants from the FIG. 1 sequence, and may represent naturally occurring alleles (which will not require manipulation of the CHF DNA) or predetermined mutant forms made by mutating the DNA, either to arrive at an allele or a variant not found in nature. In general, the location and nature of the mutation chosen will depend upon the CHF characteristic to be modified.

Amino acid sequence deletions generally range from about 1 to 30 residues, more preferably about 1 to 10 residues, and typically are contiguous. Contiguous deletions ordinarily are made in even numbers of residues, but single or odd numbers of deletions are within the scope hereof. Deletions may be introduced into regions of low homology among CHF and other ligands binding to the GH/cytokine receptor family which share the most sequence identity to the human CHF amino acid sequence to modify the activity of CHF. Deletions from CHF in areas of substantial homology with one of the receptor binding sites of other ligands that bind to the GH/cytokine receptor family will be more likely to modify the biological activity of CHF more significantly. The number of consecutive deletions will be selected so as to preserve the tertiary structure of CHF in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the mature CHF sequence) may range generally from about 1 to 10 residues, more preferably 1 to 5, most preferably 1 to 3. Insertions are preferably made in even numbers of residues, but this is not required. Examples of terminal insertions include mature CHF with an N-terminal methionyl residue, an artifact of the direct production of mature CHF in recombinant cell culture, and fusion of a heterologous N-terminal signal sequence to the N-terminus of the mature CHF molecule to facilitate the secretion of mature CHF from recombinant hosts. Such signal sequences generally will be obtained from, and thus homologous to, the intended host cell species. Suitable sequences include STII or lpp for *E. coli*, alpha factor for yeast, and viral signals such as herpes gD for mammalian cells.

Other insertional variants of the CHF molecule include the fusion to the N- or C-terminus of CHF of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published 6 Apr. 1989.

A third group of variants are amino acid substitution variants. These variants have at least one amino acid residue in the CHF molecule removed and a different residue inserted in its place. The sites of greatest interest for substitutional mutagenesis include sites identified as the active site(s) of CHF and sites where the amino acids found in the known analogues are substantially different in terms of side-chain bulk, charge, or hydrophobicity, but where there is also a high degree of sequence identity at the selected site within various animal CHF species, or where the amino acids found in known ligands that bind to members of the GH/cytokine receptor family and novel CHF are substantially different in terms of side-chain bulk, charge, or hydrophobicity, but where there also is a high degree of sequence identity at the selected site within various animal analogues of such ligands (e.g., among all the animal CNTF molecules). This analysis will highlight residues that may be involved in the differentiation of activity of the cardiac hypertrophic, anti-arrhythmic, inotropic, and neurotrophic factors, and therefore, variations at these sites may affect such activities.

Other sites of interest are those in which particular residues of the CHF obtained from various species are identical among all animal species of CHF and other ligands binding to GH/cytokine receptor family molecules, this degree of conformation suggesting importance in achieving biological activity common to these enzymes. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |

TABLE 1-continued

| Original Residue | Exemplary Substitutions | Preferred Substitutions |
|---|---|---|
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the CHF are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another. Such substituted residues also may be introduced into the conservative substitution sites or, more preferably, into the remaining (non-conserved) sites.

In one embodiment of the invention, it is desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of CHF also may be substituted, generally with serine, to improve the oxidative stability of the molecule and prevent aberrant crosslinking.

Nucleic acid molecules encoding amino acid sequence variants of CHF are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of CHF.

Oligonucleotide-mediated mutagenesis is a preferred method for preparing substitution, deletion, and insertion variants of CHF DNA. This technique is well known in the art as described by Adelman et al., *DNA*, 2: 183 (1983).

Briefly, CHF DNA is altered by hybridizing an oligonucleotide encoding the desired mutation to a DNA template, where the template is the single-stranded form of a plasmid or bacteriophage containing the unaltered or native DNA sequence of CHF. After hybridization, a DNA polymerase is used to synthesize an entire second complementary strand of the template that will thus incorporate the oligonucleotide primer, and will code for the selected alteration in the CHF DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. *Meth. Enzymol.*, 153: 3 (1987). Thus, the DNA that is to be mutated may be inserted into one of these vectors to generate single-stranded template. Production of the single-stranded template is described in Sections 4.21–4.41 of Sambrook et al., supra.

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of CHF, and the other strand (the original template) encodes the native, unaltered sequence of CHF. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}P$ to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding CHF mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of CHF. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 μL. The reaction mixture is overlayed with 35 μL mineral oil. The reaction mixture is denatured for five minutes at 100° C., placed briefly on ice, and then 1 μL Thermus aquaticus (Taq) DNA polymerase (5 units/μL, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.

30 sec. 72° C., then 19 cycles of the following:

30 sec. 94° C.

30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene,* 34: 315 (1985). The starting material is the plasmid (or other vector) comprising the CHF DNA to be mutated. The codon(s) in the CHF DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the CHF DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated CHF DNA sequence.

C. Insertion of Nucleic Acid into Replicable Vector

The nucleic acid (e.g., cDNA or genomic DNA) encoding native or variant CHF is inserted into a replicable vector for further cloning (amplification of the DNA) or for expression. Many vectors are available, and selection of the appropriate vector will depend on 1) whether it is to be used for DNA amplification or for DNA expression, 2) the size of the nucleic acid to be inserted into the vector, and 3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(i) Signal Sequence Component

The CHFs of this invention may be produced not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the CHF DNA that is inserted into the vector. The heterologous signal sequence selected should be one that is recognized and processed (i.e., cleaved by a signal peptidase) by the host cell. For prokaryotic host cells that do not recognize and process the native CHF signal sequence, the signal sequence is substituted by a prokaryotic signal sequence selected, for example, from the group consisting of the alkaline phosphatase, penicillinase, lpp, or heat-stable enterotoxin II leaders. For yeast secretion the native signal sequence may be substituted by, e.g., the yeast invertase leader, alpha factor leader (including Saccharomyces and Kluyveromyces α-factor leaders, the latter described in U.S. Pat. No. 5,010,182 issued 23 Apr. 1991), or acid phosphatase leader, the C. albicans glucoamylase leader (EP 362,179 published 4 Apr. 1990), or the signal described in WO 90/13646 published 15 Nov. 1990. In mammalian cell expression the native human signal sequence (i.e., the CHF presequence that normally directs secretion of CHF from human cells in vivo) is satisfactory, although other mammalian signal sequences may be suitable, such as signal sequences from other animal CHFs, signal sequences from a ligand binding to another GH/cytokine receptor family member, and signal sequences from secreted polypeptides of the same or related species, as well as viral secretory leaders, for example, the herpes simplex gD signal.

The DNA for such precursor region is ligated in reading frame to DNA encoding the mature CHF.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of CHF DNA. However, the recovery of genomic DNA encoding CHF is more complex than that of an exogenously replicated vector because restriction enzyme digestion is required to excise the CHF DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., *J. Molec. Appl. Genet.*, 1: 327 [1982]), mycophenolic acid (Mulligan et al., *Science*, 209: 1422 [1980]), or hygromycin (Sugden et al., *Mol. Cell. Bio.*, 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the CHF nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes CHF. Amplification is the process by which genes in greater demand for the production of a protein critical for growth are reiterated in tandem within the chromosomes of successive generations of recombinant cells. Increased quantities of CHF are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding CHF. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding CHF, wild-type DHFR protein, and another selectable marker such as aminoglycoside 3-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282: 39 [1979]; Kingsman et al., *Gene*, 7: 141 [1979]; or Tschemper et al., *Gene*, 10: 157 [1980]). The trp1 gene provides a selection marker for a mutant strain of yeast lacking the ability to grow in tryptophan, for example, ATCC No. 44076 or PEP4-1 (Jones, *Genetics*, 85: 12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Bianchi et al., *Curr. Genet.*, 12: 185 (1987). More recently, an expression system for large-scale production of recombinant calf chymosin was reported for K. lactis. Van den Berg, *Bio/Technology*, 8: 135 (1990). Stable multicopy expression vectors for secretion of mature recombinant human serum albumin by industrial strains of Kluyveromyces have also been disclosed. Fleer et al., *Bio/Technology*, 9: 968–975 (1991).

(iv) Promoter Component

Expression and cloning vectors usually contain a promoter that is recognized by the host organism and is operably linked to the CHF nucleic acid. Promoters are untranslated sequences located upstream (5') to the start codon of a structural gene (generally within about 100 to 1000 bp) that control the transcription and translation of particular nucleic acid sequence, such as the CHF nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to CHF-encoding DNA by removing the promoter from the source DNA by restriction enzyme digestion and inserting the isolated promoter sequence into the vector. Both the native CHF promoter sequence and many heterologous promoters may be used to direct amplification and/or expression of the CHF DNA. However, heterologous promoters are preferred, as they generally permit greater transcription and higher yields of recombinantly produced CHF as compared to the native CHF promoter.

Promoters suitable for use with prokaryotic hosts include the β-lactamase and lactose promoter systems (Chang e al., *Nature*, 275: 615 [1978]; and Goeddel et al., Nature, 281: 544 [1979]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. USA*, 80: 21–25 [1983]). However, other known bacterial promoters are suitable. Their nucleotide sequences have been published, thereby enabling a skilled worker operably to ligate them to DNA encoding CHF (Siebenlist et al., *Cell*, 20: 269 [1980]) using linkers or adaptors to supply any required restriction sites. Promoters for use in bacterial systems also will contain a Shine-Dalgarno (S.D.) sequence operably linked to the DNA encoding CHF.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657. Yeast enhancers also are advantageously used with yeast promoters.

CHF transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, arian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the CHF sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209: 1422–1427 (1980); Pavlakis et al., *Proc. Natl. Acad. Sci. USA*, 78: 7398–7402 (1981). The immediate early promoter of the human cytomegalovirus is conveniently obtained as a HindIII E restriction fragment. Greenaway et al., *Gene*, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells; Reyes et al., *Nature*, 297: 598–601 (1982) on expression of human β-interferon cDNA in mouse cells under the control of a thymidine kinase promoter from herpes simplex virus; Canaani and Berg, *Proc. Natl. Acad. Sci. USA*, 79: 5166–5170 (1982) on expression of the human interferon β1 gene in cultured mouse and rabbit cells; and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the CHF of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA*, 78: 993 [1981]) and 3' (Lusky et al., *Mol. Cell Bio.*, 3: 1108 [1983]) to the transcription unit, within an intron (Banerji et al., *Cell*, 33: 729 [1983]), as well as within the coding sequence itself (Osborne et al., *Mol. Cell Bio.*, 4: 1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the CHF-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding CHF.

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

(viii) Transient Expression Vectors

Particularly useful in the practice of this invention are expression vectors that provide for the transient expression in mammalian cells of DNA encoding CHF. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of CHF that are biologically active CHF.

(ix) Suitable Exemplary Vertebrate Cell Vectors

Other methods, vectors, and host cells suitable for adaptation to the synthesis of CHF in recombinant vertebrate cell culture are described in Gething et al., *Nature*, 293: 620–625 (1981); Mantei et al., *Nature*, 281: 40–46 (1979); EP 117,060; and EP 117,058. A particularly useful plasmid for mammalian cell culture production of CHF is pRK5 (EP 307,247) or pSVI6B (WO 91/08291 published 13 Jun. 1991). The pRK5 derivative pRK5B (Holmes et al., *Science*, 253: 1278–1280 [1991]) is particularly suitable herein for such expression.

D. Selection and Transformation of Host Cells

Suitable host cells for cloning or expressing the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published 12 Apr. 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), *E. coli* DH5α, and *E. coli* W3110 (ATCC 27,325) are suitable. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonAΔ; *E. coli* W3110 strain 9E4, which has the complete genotype tonAΔ ptr3; *E. coli* W3110 strain 27C7 (ATCC 55,244), which has the complete genotype tonA ptr3 phoAΔE15 Δ(argF-lac)169 ΔdegP ΔompT kan$^r$; *E. coli* W3110 strain 37D6, which has the complete genotype tonA ptr3 phoAΔE15 Δ(argF-lac)169 ΔdegP ΔompT Δrbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for CHF-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature*, 290: 140 [1981]; EP 139,383 published 2 May 1985); Kluyveromyces hosts (U.S. Pat. No. 4,943,529; Fleer et al., supra) such as, e.g., *K. lactis* (MW98-8C, CBS683, CBS4574; Louvencourt et al., *J. Bacteriolo*, 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; yarrowia (EP 402,226); *Pichia pastoris* (EP 183,070; Sreekrishna et al., *J. Basic Microbiol.*, 28: 265–278 [1988]); Candida; *Trichoderma reesia* (EP 244,234); *Neurospora crassa* (Case et al., *Proc. Natl. Acad. Sci. USA*, 76: 5259–5263 [1979]); Schwanniomyces such as *Schwanniomyces occidentalis* (EP 394,538 published 31 Oct. 1990); and filamentous fungi such as, e.g., Neurospora, Penicillium, Tolypocladium (WO 91/00357 published 10 Jan. 1991), and Aspergillus hosts such as *A. nidulans* (Ballance et al., *Biochem. Biophys. Res. Commun.*, 112: 284–289 [1983]; Tilburn et al., *Gene*, 26: 205–221 [1983]; Yelton et al., *Proc. Natl. Acad. Sci. USA*, 81: 1470–1474 [1984]) and *A. niger* (Kelly and Hynes, *EMBO J.*, 4: 475–479 [1985]).

Suitable host cells for the production of CHF are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47–55 (1988); Miller et al., in *Genetic Engineering*, Setlow, J. K. et al., eds., Vol. 8 (Plenum Publishing, 1986), pp. 277–279; and Maeda et al., *Nature*, 315: 592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically plant cells are transfected by incubation with certain strains of the bacterium *Agrobacterium tumefaciens*, which has been previously manipulated to contain the CHF DNA. During incubation of the plant cell culture with *A. tumefaciens*, the DNA encoding the CHF is transferred to the plant cell host such that it is transfected, and will, under appropriate conditions, express the CHF DNA. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure in recent years (*Tissue Culture*, Academic Press, Kruse and Patterson, editors [1973]). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 [1977]); baby hamster kidney cells (BHK, ATCC CCL 10); Chinese hamster ovary cells/-DHFR (CHO, Urlaub and Chasin, *Proc. Natl. Acad. Sci. USA*, 77: 4216 [1980]); mouse sertoli cells (TM4, Mather, *Biol. Reprod.*, 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); TRI cells (Mather et al., *Annals N.Y. Acad. Sci.*, 383: 44–68 [1982]); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology*, 52: 456–457 (1978) is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology*, 185: 527–537 (1990) and Mansour et al., *Nature*, 336: 348–352 (1988).

E. Culturing the Host Cells

Prokaryotic cells used to produce the CHF polypeptide of this invention are cultured in suitable media as described generally in Sambrook et al., supra.

The mammalian host cells used to produce the CHF of this invention may be cultured in a variety of media. Commercially available media such as Ham's F-10 (Sigma), F-12 (Sigma), Minimal Essential Medium ([MEM], Sigma), RPMI-1640 (Sigma), Dulbecco's Modified Eagle's Medium ([D-MEM], Sigma), and D-MEM/F-12 (Gibco BRL) are suitable for culturing the host cells. In addition, any of the media described, for example, in Ham and Wallace, *Methods in Enzymology*, 58: 44 (1979); Barnes and Sato, *Anal. Biochem.*, 102: 255 (1980); U.S. Pat. Nos. 4,767,704; 4,657,866; 4,927,762; 5,122,469; or 4,560,655; U.S. Pat. No. Re. 30,985; WO 90/03430; or WO 87/00195 may be used as culture media for the host cells. Any of these media may be supplemented as necessary with hormones and/or other growth factors (such as insulin, transferrin, aprotinin, and/or epidermal growth factor [EGF]), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vitro mammalian cell cultures can be found in *Mammalian Cell Biotechnology: a Practical Approach*, M. Butler, ed. (IRL Press, 1991).

The host cells referred to in this disclosure encompass cells in in vitro culture as well as cells that are within a host animal.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77: 5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal, and may be prepared in any mammal. Conveniently, the antibodies may be prepared against a native CHF polypeptide or against a synthetic peptide based on the DNA sequences provided herein as described further in Section 4 below.

G. Purification of CHF Polypeptide

CHF preferably is recovered from the culture medium as a secreted polypeptide, although it also may be recovered from host cell lysates when directly produced without a secretory signal.

When CHF is produced in a recombinant cell other than one of human origin, the CHF is completely free of proteins or polypeptides of human origin. However, it is necessary to purify CHF from cell proteins or polypeptides to obtain preparations that are substantially homogeneous as to CHF. As a first step, the particulate debris, either host cells or lysed fragments, is removed, for example, by centrifugation or ultrafiltration; optionally, the protein may be concentrated with a commercially available protein concentration filter, followed by separating the CHF from other impurities by one or more steps selected from immunoaffinity chromatography, ion-exchange column fractionation (e.g., on DEAE or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using e.g., Sephadex molecular sieve or size-exclusion chromatography, chromatography on columns that selectively bind the CHF, and ethanol or ammonium sulfate precipitation. A protease inhibitor such as methylsulfonylfluoride (PMSF) may be included in any of the foregoing steps to inhibit proteolysis.

A preferred purification scheme involves adjusting the culture medium conditioned by cells transfected with the relevant clone to 1.5M NaCl and applying to a Butyl Toyopearl™ column. The column is washed with Tris[hydroxymethyl]aminomethane hydrochloride (TRIS-HCl), pH 7.5, containing NaCl, and the activity eluted with TRIS-HCl, pH 7.5, containing 10 mM Zwittergent™ 3–10 surfactant. The peak of activity is adjusted to 150 mM NaCl, pH 8.0, and applied to a MONO-Q Fast Flow column. This column is washed with TRIS-HCl, pH 8.0, containing NaCl and octyl glucoside. Activity is found in the flow-through fraction. The active material is then applied to a reverse phase C4 column in 0.1% TFA, 10% acetonitrile, and eluted with a gradient of 0.1% TFA up to 80%. The activity fractionates at about 15–30 kDa on gel filtration columns. It is expected that a chaotrope such as guanidine-HCl, is required for resolution and recovery.

CHF variants in which residues have been deleted, inserted, or substituted are recovered in the same fashion as native CHF, taking account of any substantial changes in properties occasioned by the variation. For example, preparation of a CHF fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-CHF column can be employed to absorb the CHF variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native CHF may require modification to account for changes in the character of CHF or its variants upon production in recombinant cell culture.

H. Covalent Modifications of CHF Polypeptides

Covalent modifications of CHF polypeptides are included within the scope of this invention. Both native CHF and amino acid sequence variants of the CHF may be covalently modified. One type of covalent modification included within the scope of this invention is a CHF fragment. Variant CHF fragments having up to about 40 amino acid residues may be conveniently prepared by chemical synthesis or by enzymatic or chemical cleavage of the full-length or variant CHF polypeptide. Other types of covalent modifications of the CHF or fragments thereof are introduced into the molecule by reacting targeted amino acid residues of the CHF or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking CHF to a water-insoluble support matrix or surface for use in the method for purifying anti-CHF antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group.

Another type of covalent modification of the CHF polypeptide included within the scope of this invention comprises altering the native glycosylation pattern of the polypeptide. By altering is meant deleting one or more carbohydrate moieties found in native CHF, and/or adding one or more glycosylation sites that are not present in the native CHF.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the CHF polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native CHF sequence (for O-linked glycosylation sites). For ease, the CHF amino acid sequence is preferably altered through changes at the DNA level, particularly by mutating the DNA encoding the CHF polypeptide at preselected bases such that codons are generated that will translate into the desired amino acids. The DNA mutation(s) may be made using methods described above under Section 2B.

Another means of increasing the number of carbohydrate moieties on the CHF polypeptide is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.,* pp. 259–306 (1981).

Removal of any carbohydrate moieties present on the CHF polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.,* 259: 52 (1987) and by Edge et al., *Anal. Biochem.,* 118: 131 (1981). Enzymatic cleavage of carbohydrate moieties on polypeptides can be achieved by the use of a variety of endo- and exo-glycosidases as described by Thotakura et al., *Meth. Enzymol.,* 138: 350 (1987).

Glycosylation at potential glycosylation sites may be prevented by the use of the compound tunicamycin as described by Duskin et al., *J. Biol. Chem.,* 257: 3105 (1982). Tunicamycin blocks the formation of protein-N-glycoside linkages.

Another type of covalent modification of CHF comprises linking the CHF polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

CHF also may be entrapped in microcapsules prepared, for example, by coacervation techniques or by interfacial polymerization (for example, hydroxymethylcellulose or gelatinmicrocapsules and poly-[methylmethacylate]microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

CHF preparations are also useful in generating antibodies, as standards in assays for CHF (e.g., by labeling CHF for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Since it is often difficult to predict in advance the characteristics of a variant CHF; it will be appreciated that some screening of the recovered variant will be needed to select the optimal variant. One can screen for enhanced cardiac hypertrophic, anti-arrhythmic, inotropic, or neurotrophic activity, possession of CHF antagonist activity, increased expression levels, oxidative stability, ability to be secreted in elevated yields, and the like. For example, a change in the immunological character of the CHF molecule, such as affinity for a given antibody, is measured by a competitive-type immunoassay. The variant is assayed for changes in the suppression or enhancement of its hypertrophic, anti-arrhythmic, inotropic, and neurotrophic activities by comparison to the respective activities observed for native CHF in the same assay (using, for example, the hypertrophy and neurotrophic assays described in the examples below.) Other potential modifications of protein or polypeptide properties such as redox or thermal stability, hydrophobicity, susceptibility to proteolytic degradation, or the tendency to aggregate with carriers or into multimers are assayed by methods well known in the art.

I. Antagonists of CHF

Antagonists to CHF can be prepared by using the predicted family of receptors for CHF (the GH/cytokine receptor family, including the CNTF, LIF, and oncostatin M receptor subfamily). Thus, the receptor can be expression cloned from the family; then a soluble form of the receptor is made by identifying the extracellular domain and excising the transmembrane domain therefrom. The soluble form of the receptor can then be used as an antagonist, or the receptor can be used to screen for small molecules that would antagonize CHF activity.

Alternatively, using the sequence shown in FIG. 1 or the human sequence, variants of CHF are made that act as antagonists. Since the GH/cytokine receptor family is known to have two binding sites on the ligand, the receptor binding sites of CHF can be determined by binding studies and one of them eliminated by standard techniques (deletion or radical substitution) so that the molecule acts as an antagonist.

Antagonist activity can be determined by several means, including the hypertrophy and neurotrophic assays described herein.

J. Hypertrophy Assay

A miniatured assay is preferably used to assay for hypertrophic activity. In this assay the medium used allows the cells to survive at a low plating density without serum. By plating directly into this medium, washing steps are eliminated so that fewer cells are removed. The plating density is important: many fewer cells and the survival is reduced; many more cells and the myocytes begin to self-induce hypertrophy.

The steps involved are:

(a) plating 96-well plates with a suspension of myocytes at a cell density of about $7.5 \times 10^4$ cells per mL in D-MEM/F-12 medium supplemented with at least insulin, transferrin, and aprotinin;

(b) culturing the cells;

(c) adding a substance to be assayed (such as one suspected of containing a CHF);

(d) culturing the cells with the substance; and (e) measuring for hypertrophy.

The medium can be supplemented with additional elements such as EGF that ensure a longer viability of the cells, but such supplements are not essential. D-MEM/F-12 medium is available from Gibco BRL, Gaithersburg, Md., and consists of one of the following media:

| Component | 11320 1× Liquid (mg/L) | 11321 1× Liquid (mg/L) | 11330 1× Liquid (mg/L) | 11331 1× Liquid (mg/L) | 12400 Powder (mg/L) | 12500 Powder (mg/L) |
|---|---|---|---|---|---|---|
| AMINO ACIDS: | | | | | | |
| L-Alanine | 4.45 | 4.45 | 4.45 | 4.45 | 4.45 | 4.45 |
| L-Arginine .HCl | 147.50 | 147.50 | 147.50 | 147.50 | 147.50 | 147.50 |
| L-Asparagine .H₂O | 7.50 | 7.50 | 7.50 | 7.50 | 7.50 | 7.50 |
| L-Aspartic acid | 6.65 | 6.65 | 6.65 | 6.65 | 6.65 | 6.65 |
| L-Cysteine .HCl .H₂O | 17.56 | 17.56 | 17.56 | 17.56 | 17.56 | 17.56 |
| L-Cystine .2HCl | 31.29 | 31.29 | 31.29 | 31.29 | 31.29 | 31.29 |
| L-Glutamic acid | 7.35 | 7.35 | 7.35 | 7.35 | 7.35 | 7.35 |
| L-Glutamine | 365.00 | 365.00 | 365.00 | 365.00 | 365.00 | 365.00 |
| Glycine | 18.75 | 18.75 | 18.75 | 18.75 | 18.75 | 18.7S |
| L-Histidine .HCl .H₂O | 31.48 | 31.48 | 31.48 | 31.48 | 31.48 | 31.48 |
| L-Isoleucine | 54.47 | 54.47 | 54.47 | 54.47 | 54.47 | 54.47 |
| L-Leucine | 59.05 | 59.05 | 59.05 | 59.05 | 59.OS | 59.05 |
| L-Lysine .HCl | 91.25 | 91.25 | 91.25 | 91.25 | 91.25 | 91.25 |
| L-Methionine | 17.24 | 17.24 | 17.24 | 17.24 | 17.24 | 17.24 |
| L-Phenylalanine | 35.48 | 35.48 | 35.48 | 35.48 | 35.48 | 35.48 |
| L-Proline | 17.25 | 17.25 | 17.25 | 17.25 | 17.25 | 17.25 |
| L-Serine | 26.25 | 26.25 | 26.25 | 26.25 | 26.25 | 26.25 |
| L-Threonine | 53.45 | 53.45 | 53.45 | 53.45 | 53.45 | 53.45 |
| L-Tryptophan | 9.02 | 9.02 | 9.02 | 9.02 | 9.02 | 9.02 |
| L-Tyrosine .2Na .2H₂O | 55.79 | 55.79 | 55.79 | 55.79 | 55.79 | 55.79 |
| L-Valine | 52.85 | 52.85 | 52.85 | 52.85 | 52.85 | 52.85 |
| INORGANIC SALTS: | | | | | | |
| CaCl₂ anhyd. | 116.60 | 116.60 | 116.60 | 116.60 | 116.60 | 116.60 |
| CuSO₄ .5H₂O | 0.0013 | 0.0013 | 0.0013 | 0.0013 | 0.0013 | 0.0013 |
| Fe(NO₃)₃ | 0.05 | 0.05 | 0.05 | 0.05 | 0.05 | 0.05 |

| Component | 11320 1× Liquid (mg/L) | 11321 1× Liquid (mg/L) | 11330 1× Liquid (mg/L) | 11331 1× Liquid (mg/L) | 12400 Powder (mg/L) | 12500 Powder (mg/L) |
|---|---|---|---|---|---|---|
| .9H$_2$O | | | | | | |
| FeSO$_4$.7H$_2$O | 0.417 | 0.417 | 0.417 | 0.417 | 0.417 | 0.417 |
| KCl | 311.80 | 311.80 | 311.80 | 311.80 | 311.80 | 311.80 |
| MgCl$_2$ | 28.64 | 28.64 | 28.64 | 28.64 | 28.64 | 28.64 |
| MgSO$_4$ | 48.84 | 48.84 | 48.84 | 48.84 | 48.84 | 48.84 |
| NaCl | 6999.50 | 6999.50 | 6999.50 | 6999.50 | 6999.50 | 6999.50 |
| NaHCO$_3$ | 2438.00 | 2438.00 | 2438.00 | 2438.00 | — | — |
| NaH$_2$PO$_4$.H$_2$O | 62.50 | 62.50 | 62.50 | — | 62.50 | 62.50 |
| Na$_2$HPO$_4$ | 71.02 | 71.02 | 71.02 | — | 71.02 | 71.02 |
| ZnSO$_4$.7H$_2$O | 0.432 | 0.432 | 0.432 | 0.432 | 0.432 | 0.432 |
| OTHER COMPONENTS: | | | | | | |
| D-Glucose | 3151.00 | 3151.00 | 3151.00 | 3151.00 | 3151.00 | 3151.00 |
| HEPES | — | — | 3574.50 | 3574.50 | 3574.50 | — |
| Na hypoxanthine | 2.39 | 2.39 | 2.39 | 2.39 | 2.39 | 2.39 |
| Linoleic acid | 0.042 | 0.042 | 0.042 | 0.042 | 0.042 | 0.042 |
| Lipoic acid | 0.105 | 0.105 | 0.105 | 0.105 | 0.105 | 0.105 |
| Phenol red | 8.10 | 8.10 | 8.10 | 8.10 | 8.10 | 8.10 |
| Putrescine.2H$_2$O | 0.081 | 0.081 | 0.081 | 0.081 | 0.081 | 0.081 |
| Sodium pyruvate | 55.00 | 55.00 | 55.00 | 55.00 | 55.00 | 55.00 |
| VITAMINS: | | | | | | |
| Biotin | 0.0035 | 0.0035 | 0.0035 | 0.0035 | 0.0035 | 0.0035 |
| D-Ca pantothenate | 2.24 | 2.24 | 2.24 | 2.24 | 2.24 | 2.24 |
| Choline chloride | 8.98 | 8.98 | 8.98 | 8.98 | 8.98 | 8.98 |
| Folic acid | 2.65 | 2.65 | 2.65 | 2.65 | 2.65 | 2.65 |
| i-Inositol | 12.60 | 12.60 | 12.60 | 12.60 | 12.60 | 12.60 |
| Niacinamide | 2.02 | 2.02 | 2.02 | 2.02 | 2.02 | 2.02 |
| Pyridoxal.HCl | 2.00 | — | 2.00 | — | 2.00 | 2.00 |
| Pyridoxine.HCl | 0.031 | 2.031 | 0.031 | 2.031 | 0.031 | 0.031 |
| Riboflavin | 0.219 | 0.219 | 0.219 | 0.219 | 0.219 | 0.219 |
| Thiamine.HCl | 2.17 | 2.17 | 2.17 | 2.17 | 2.17 | 2.17 |
| Thymidine | 0.365 | 0.365 | 0.365 | 0.365 | 0.365 | 0.365 |
| Vitamin B$_{12}$ | 0.68 | 0.68 | 0.68 | 0.68 | 0.68 | 0.68 |

The preferred hypertrophy assay comprises:

(a) precoating the wells of 96-well tissue culture plates with a medium containing calf serum, preferably D-MEM/F-12 medium containing 4% fetal calf serum, wherein preferably the wells are incubated with the medium for about eight hours at about 37° C.;

(b) removing the medium;

(c) plating a suspension of myocytes in the inner 60 wells at 7.5×10$^4$ cells per mL in D-MEM/F-12 medium supplemented with insulin, transferrin, and aprotinin;

(d) culturing the myocytes for at least 24 hours;

(e) adding the test substance;

(f) culturing the cells with the test substance (preferably for about 24–72 hours, more preferably for about 48 hours); and (g) measuring for hypertrophy, preferably with crystal violet stain.

Preferably the medium used in step (c) is a serum-free medium also containing penicillin/streptomycin (pen/strep) and glutamine. Most preferably, the medium contains 100 mL D-MEM/F-12, 100 μL transferrin (10 mg/mL), 20 μL insulin (5 mg/mL), 50 μL aprotinin (2 mg/mL), 1 mL pen/strep (JRH Biosciences No. 59602-77P), and 1 mL L-glutamine (200 mM).

The assay capacity of 1000 single samples a week coupled with the small sample size requirement of 100 μL or less has enabled an expression cloning and protein purification that would have been impossible to accomplish using the current methods available.

Another method for assaying hypertrophy involves measuring for atrial natriuretic peptide (ANP) release by means of an assay that determines the competition for binding of $^{125}$I-rat ANP for a rat ANP receptor A-IgG fusion protein. The method suitable for use is similar to that used for determining gp120 using a CD4-IgG fusion protein described by Chamow et al., *Biochemistry*, 29: 9885–9891 (1990).

K. Neurotrophic Assay

The assay used for ciliary ganglion neurotrophic activity described in Leung, *Neuron,* 8: 1045–1053 (1992) is suitable herein. Briefly, ciliary ganglia are dissected from E7–E8 chick embryos and dissociated in trypsin-EDTA (Gibco 1540Q–013) diluted ten fold in phosphate-buffered saline for 15 minutes at 37° C. The ganglia are washed free of trypsin with three washes of growth medium (high glucose D-MEM supplemented with 10% fetal bovine serum, 1.5 mM glutamine, 100 µg/mL penicillin, and 100 g/mL strepomycin), and then gently triturated in 1 mL of growth medium into a single-cell suspension. Neurons are enriched by plating this cell mixture in 5 mL of growth media onto a 100-mm tissue culture dish for 4 hours at 37° C. in a tissue culture incubator. During this time the non-neuronal cells preferentially stick to the dish and neurons can be gently washed free at the end of the incubation. The enriched neurons are then plated into a 96-well plate previously coated with collagen. In each well, 1000 to 2000 cells are plated, in a final volume of 100 to 250 µL, with dilutions of the CHF to be tested. Following a 2–4-day incubation at 37° C., the number of live cells is assessed by staining live cells using the vital dye metallothionine (MTT). One-fifth of the volume of 5 mg/mL MTT (Sigma M2128) is added to the wells. After a 2–4-hour incubation at 37° C., live cells (filled with a dense purple precipitate) are counted by phase microscopy at 100× magnification.

3. Uses and Therapeutic Compositions and Administration of CHF

CHF is believed to find use as a drug for treatment of mammals (e.g., animals or humans) in vivo having heart failure, arrhythmic or inotropic disorders, and/or peripheral neuropathies and other neurological disorders involving motor neurons or other neurons in which CNTF is active. For example, CHF may be useful in treating congestive heart failure in cases where ACE inhibitors cannot be employed or are not as effective. CHF optionally is combined with or administered in concert with other agents for treating congestive heart failure, including ACE inhibitors.

CHF is also potentially useful in the generation, maturation, and survival of oligodendrocytes in vitro for protection of oligodendrocytes against natural and tumor necrosis factor-induced death; in the survival and differentiation of astrocytes and the induction of type-2 astrocyte development, and in the stimulation of the recombinant production of low-affinity nerve growth factor receptor and CD-4 by rat central nervous system (CNS) microglia.

CHF is also potentially useful in having a trophic effect on denervated skeletal muscle. In addition, it is expected to have the proliferative responses and binding properties of hematopoietic cells transfected with low-affinity receptors for leukemia inhibitory factor, oncostatin M, and ciliary neurotrophic factor, to regulate fibrinogen gene expression in hepatocytes by binding to the interleukin-6 receptor, to have trophic actions on murine embryonic carcinoma cells, to be an endogenous pyrogen, and to have a mitogenic effect on human IMR 32 neuroblastoma cells.

In addition, CHF is expected to enhance the response to nerve growth factor of cultured rat sympathetic neurons, to maintain motoneurons and their target muscles in developing rats, to induce motor neuron sprouting in vitro, to promote the survival of neonatal rat corticospinal neurons in vitro, to prevent degeneration of adult rat substantia nigra dopaminergic neurons in vivo, to alter the threshold of hippocampal pyramidal neuron sensitivity to excitotoxin damage, to prevent neuronal degeneration and promote low-affinity NGF receptor production in the adult rat CNS, and to enhance neuronal survival in embryonic rat hippocampal cultures.

These activities translate into the treatment of all neurodegenerative diseases by CHF, including peripheral neuropathies (motor and sensory), ALS, Alzheimer's disease, Parkinson's disease, stroke, Huntington's disease, and ophthalmologic diseases, for example, those involving the retina.

CHF may also be useful as an adjunct treatment of neurological disorders together with such neurotrophic factors as, e.g., CNTF, NGF, BDNF, NT-3, NT-4, and NT-5.

The nucleic acid encoding the CHF may be used as a diagnostic for tissue-specific typing. For example, such procedures as in situ hybridization, northern and Southern blotting, and PCR analysis may be used to determine whether DNA and/or RNA encoding CHF is present in the cell type(s) being evaluated.

Isolated CHF polypeptide may also be used in quantitative diagnostic assays as a standard or control against which samples containing unknown quantities of CHF may be prepared.

Therapeutic formulations of CHF for treating heart failure and neurological disorders are prepared for storage by mixing CHF having the desired degree of purity with optional physiologically acceptable carriers, excipients or stabilizers (*Remington's Pharmaceutical Sciences,* supra), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

CHF to be used for in vivo administration must be sterile. This is readily accomplished by filtration through sterile filtration membranes, prior to or following lyophilization and reconstitution. CHF ordinarily will be stored in lyophilized form or in solution.

Therapeutic CHF compositions generally are placed into a container having a sterile access port, for example, an intravenous solution bag or vial having a stopper pierceable by a hypodermic injection needle.

The route of CHF or CHF antibody administration is in accord with known methods, e.g., injection or infusion by intravenous, intraperitoneal, intracerebral, intramuscular, intraocular, intraarterial, or intralesional routes, or by sustained-release systems as noted below. CHF is administered continuously by infusion or by bolus injection. CHF antibody is administered in the same fashion, or by administration into the blood stream or lymph.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethylmethacrylate) as described by Langer et al., *J. Biomed. Mater. Res.,* 15: 167–277 [1981] and Langer, *Chem. Tech.,* 12: 98–105 [1982] or poly(vinylalcohol)), polylactides (U.S. Pat. No. 3,773,919, EP 58,481), copolymers of L-glutamic acid and gamma ethyl-L-glutamate (Sidman et al., *Biopolymers,* 22: 547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133, 988).

While polymers such as ethylene-vinyl acetate and lactic acidglycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release CHF compositions also include liposomally entrapped CHF. Liposomes containing CHF are prepared by methods known per se: DE 3,218,121; Epstein et al., *Proc. Natl. Acad. Sci. USA,* 82: 3688–3692 (1985); Hwang et al., *Proc. Natl. Acad. Sci. USA,* 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal CHF therapy.

An effective amount of CHF to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg of patient body weight or more per day, depending on the factors mentioned above, preferably about 10 µg/kg/day to 10 mg/kg/day. Typically, the clinician will administer CHF until a dosage is reached that achieves the desired effect for treatment of the heart or neural disfunction. For example, the amount would be one which increases ventricular contractility and decreases peripheral vascular resistance or ameliorates or treats conditions of similar importance in congestive heart failure patients. The progress of this therapy is easily monitored by conventional assays.

4. CHF Antibody Preparation (i) Polyclonal antibodies

Polyclonal antibodies to CHF polypeptides or fragments are generally raised in animals by multiple subcutaneous (sc) or intraperitoneal (ip) injections of CHF and an adjuvant. It may be useful to conjugate CHF or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the CHF polypeptide or fragment, immunogenic conjugates, or derivatives by combining 1 mg of 1 µg of the peptide or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for CHF antibody titer. Animals are boosted until the titer plateaus. Preferably, the animal is boosted with the conjugate of the same CHF, but conjugated to a different protein and/or through a different cross-linking reagent. Conjugates also can be made in recombinant cell culture as protein fusions. Also, aggregating agents such as alum are suitably used to enhance the immune response.

(ii) Monoclonal antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the CHF monoclonal antibodies of the invention may be made using the hybridoma method first described by Kohler and Milstein, *Nature,* 256: 495 (1975), or may be made by recombinant DNA methods (Cabilly et al., supra).

In the hybridoma method, a mouse or other appropriate host animal, such as hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59–103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.,* 133: 3001 [1984]; Brodeur et al., *Monoclonal Antibody Production Techniques and Applications,* pp. 51–63 [Marcel Dekker, Inc., New York, 1987]).

Culture medium in which hybridoma cells are growing is assayed for production of monoclonal antibodies directed against CHF. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, *Anal. Biochem.*, 107: 220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5: 256–262 (1993) and Plückthun, *Immunol. Revs.*, 130:151–188 (1992). The DNA also may be modified, for example, by substituting the coding sequence for human heavy- and light-chain constant domains in place of the homologous murine sequences (Cabilly et al., supra; Morrison, et al., *Proc. Nat. Acad. Sci.*, 81: 6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a CHF and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the antibody to the detectable moiety may be employed, including those methods described by Hunter et al., *Nature*, 144: 945 (1962); David et al., *Biochemistry*, 13: 1014 (1974); Pain et al., *J. Immunol. Meth.*, 40: 219 (1981); and Nygren, *J. Histochem. and Cytochem.*, 30: 407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147–158 (CRC Press, Inc., 1987).

Competitive binding assays rely on the ability of a labeled standard (which may be a CHF or an immunologically reactive portion thereof) to compete with the test sample analyte (CHF) for binding with a limited amount of antibody. The amount of CHF in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein (CHF) to be detected. In a sandwich assay, the test sample analyte is bound by a first antibody which is immobilized on a solid support, and thereafter a second antibody binds to the analyte, thus forming an insoluble three-part complex. David and Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme (e.g., horseradish peroxidase).

(iii) Humanized and human antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321: 522–525 [1986]; Riechmann et al., *Nature*, 332: 323–327 [1988]; Verhoeyen et al., *Science*, 239: 1534–1536 [1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151: 2296 [1993]; Chothia and Lesk, *J. Mol. Biol.*, 196: 901 [1987]). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89: 4285 [1992]; Presta et al., *J. Immnol.*, 151: 2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90: 2551–255 (1993); Jakobovits et al., *Nature*, 362: 255–258 (1993); Bruggermann et al., *Year in Immuno.*, 7: 33 (1993). Human antibodies can also be produced in phagedisplay libraries (Hoogenboom and Winter, *J. Mol. Biol.*, 227: 381 [1991]; Marks et al., *J. Mol. Biol.*, 222: 581 [1991]).

(iv) Bispecific antibodies

Bispecific antibodies are monoclonal, preferably human or humanized, antibodies that have binding specificities for at least two different antigens. Methods for making bispecific antibodies are known in the art.

Traditionally, the recombinant production of bispecific antibodies is based on the co-expression of two immunoglobulin heavy chain-light chain pairs, where the two heavy chains have different specificities (Milstein and Cuello, *Nature*, 305: 537–539 [1983]). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published 13 May 1993, and in Traunecker et al., *EMBO J.*, 10: 3655–3659 (1991).

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

For further details of generating bispecific antibodies, see, for example, Suresh et al., *Methods in Enzymology*, 121: 210 (1986).

(v) Heteroconjugate antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/00373; and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

5. Uses of CHF Antibodies

CHF antibodies are useful in diagnostic assays for CHF, e.g., its production in specific cells, tissues, or serum. The antibodies are labeled in the same fashion as CHF described above and/or are immobilized on an insoluble matrix. In one embodiment of a receptor-binding assay, an antibody composition that binds to all or a selected plurality of members of the CHF family is immobilized on an insoluble matrix, the test sample is contacted with the immobilized antibody composition to adsorb all CHF family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

The antibodies of this invention are also useful in passively immunizing patients.

CHF antibodies also are useful for the affinity purification of CHF from recombinant cell culture or natural sources. CHF antibodies that do not detectably cross-react with the rat CHF can purify CHF free from such protein.

Suitable diagnostic assays for CHF and its antibodies are well known per se. In addition to the bioassays described in the examples below wherein the candidate CHF is tested to see if it has hypertrophic, anti-arrhythmic, inotropic, or neurotrophic activity, competitive, sandwich and steric inhibition immunoassay techniques are useful. The competitive and sandwich methods employ a phaseseparation step as an integral part of the method while steric inhibition assays are conducted in a single reaction mixture. Fundamentally, the same procedures are used for the assay of CHF and for substances that bind CHF, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell-surface receptors, or antigens.

Analytical methods for CHF or its antibodies all use one or more of the following reagents: labeled analyte analogue, immobilized analyte analogue, labeled binding partner, immobilized binding partner, and steric conjugates. The labeled reagents also are known as "tracers."

The label used (and this is also useful to label CHF nucleic acid for use as a probe) is any detectable functionality that does not interfere with the binding of analyte and its binding partner. Numerous labels are known for use in immunoassay, examples including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$; fluorophores such as rare earth chelates or fluorescein and its derivatives; rhodamine and its derivatives; dansyl; umbelliferone; luciferases, e.g., firefly luciferase and bacterial luciferase (U.S. Pat. No. 4,737,456); luciferin; 2,3-dihydrophthalazinediones; malate dehydrogenase; urease; peroxidase such as horseradish peroxidase (HRP); alkaline phosphatase; β-galactosidase; glucoamylase; lysozyme; saccharide oxidases, e.g., glucose oxidase, galactose oxidase, and glucose-6-phosphate dehydrogenase; heterocyclic oxidases such as uricase and xanthine oxidase, coupled with an enzyme that employs hydrogen peroxide to oxidize a dye precursor such as HRP, lactoperoxidase, or microperoxidase; biotin/avidin; spin labels; bacteriophage labels; stable free radicals; and the like.

Those of ordinary skill in the art will know of other suitable labels that may be employed in accordance with the present invention. The binding of these labels to CHF, antibodies, or fragments thereof can be accomplished using standard techniques commonly known to those of ordinary skill in the art. For instance, coupling agents such as dialdehydes, carbodiimides, dimaleimides, bis-imidates, bis-diazotized benzidine, and the like may be used to tag the polypeptide with the above-described fluorescent, chemiluminescent, and enzyme labels. See, for example, U.S. Pat. Nos. 3,940,475 (fluorimetry) and 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); Nygren, *J. Histochem. and Cytochem.*, 30: 407–412 (1982); O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147–166; Kennedy et al., *Clin. Chim. Acta*, 70: 1–31 (1976); and Schurs et al., *Clin. Chim. Acta*, 81: 1–40 (1977). Coupling techniques mentioned in the lattermost reference are the glutaraldehyde method, the periodate method, the dimaleimide method, and the m-maleimidobenzyl-N-hydroxysuccinimide ester method.

In the practice of the present invention, enzyme labels are a preferred embodiment. No single enzyme is ideal for use as a label in every conceivable assay. Instead one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the assays of the present invention are alkaline phosphatase, HRP, beta-galactosidase, urease, glucose oxidase, glucoamylase, malate dehydrogenase, and glucose-6-phosphate dehydrogenase. Urease is among the more preferred enzyme labels, particularly because of chromogenic pH indicators that make its activity readily visible to the naked eye.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, CHF or its immunologically active fragments are conjugated with a bifunctional organic bridge to an enzyme such as peroxidase. Conjugates are selected for use with anti-CHF so that binding of the anti-CHF inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of CHF or CHF antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-CHF monoclonal antibody as one antibody and a polyclonal anti-CHF antibody as the other is useful in testing samples for CHF activity.

The foregoing are merely exemplary diagnostic assays for CHF and antibodies. Other methods now or hereafter developed for the determination of these analytes are included within the scope hereof, including the bioassays described above.

The following examples are offered by way of illustration and not by way of limitation. The disclosures of all citations in the specification are expressly incorporated herein by reference.

EXAMPLE I

Identification and In Vitro Activity of a CHF

A. Assay for Expression-Cloned Material

The assay used for hypertrophy is an in vitro neonatal rat heart hypertrophy assay described in general as follows:

1. Preparation of the Myocyte Cell Suspension

The preparation of the myocyte cell suspension is based on methods outlined in Chien et al., *J. Clin. Invest.*, 75: 1770–1780 (1985) and Iwaki et al., supra. Ventricles from the hearts of 1–2 day Sprague-Dawley rat pups were removed and trisected. The minced ventricles were digested with a series of sequential collagenase treatments. Purification of the resulting single-cell suspension on a discontinuous Percoll gradient resulted in a suspension of 95% pure myocytes.

2. Plating and Culture of the Myocytes

Two published methods for plating and culturing the myocytes are as follows: (1) Long et al., supra, preplated the cell suspension for 30 min. in MEM/5% calf serum. The unattached myocytes were then plated in serum-free MEM supplemented with insulin, transferrin, BrdU, and bovine serum albumin in 35-mm tissue-culture dishes at a density of $7.5 \times 10^4$ cells per mL. (2) Iwaki et al., supra, plated the cell suspension in D-MEM/199/5% horse serum/5% fetal calf serum in 10-cm tissue-culture dishes at $3 \times 10^5$ cells per mL. After 24 hr in culture the cells were washed and incubated in serum-free D-MEM/199.

A different protocol has been developed in accordance with this invention for plating and culturing these cells to increase testing capacity with a miniaturized assay. The wells of 96-well tissue-culture plates are precoated with D-MEM/F12/4% fetal calf serum for 8 hr at 37° C. This medium is removed and the cell suspension is plated in the inner 60 wells at $7.5 \times 10^4$ cells per mL in D-MEM/F-12 supplemented with insulin, transferrin, and aprotinin. The medium typically also contains an antibiotic such as penicillin/streptomycin and glutamine. This medium allows these cells to survive at this low plating density without serum. Test substances are added directly into the wells after the cells have been in culture for 24 hours.

3. Readout of Hypertrophy

After stimulation with alpha adrenergic agonists or endothelin, neonatal rat myocardial cells in culture display several features of the in vivo cardiac muscle cell hypertrophy seen in congestive heart failure, including an increase in cell size and an increase in the assembly of an individual contractile protein into organized contractile units. Chien et al., *FASEB J.*, supra. These changes can be viewed with an inverted phase microscope and the degree of hypertrophy scored with an arbitrary scale of 7 to 0, with 7 being fully hypertrophied cells and 3 being non-stimulated cells. The 3 and 7 states may be seen in Simpson et al., *Circulation Research*, 51: 787–801 (1982), FIG. 2, A and B, respectively. To facilitate the microscopic readout of the 96-well cultures and to generate a permanent record, the myocytes are fixed and stained after the appropriate testing period with crystal violet stain in methanol. Crystal violet is a commonly used protein stain for cultured cells.

Additionally, an aliquot can be taken from the 96-well plates and monitored for the expression of protein markers of the response such as release of ANF or ANP.

B. Expression Cloning

Poly(A)$^+$ RNA was isolated (Aviv and Leder, *Proc. Natl. Acad. Sci. USA*, 69: 1408–1412 [1972]; Cathala et al., *DNA*, 2: 329–335 [1983]) from day 7 mouse embryoid bodies. Embryoid bodies were generated by the differentiation of pluripotent embryonic stem (ES) cells (Doetschman et al., *J. Embryol. Exp. Morphol.*, 87: 27–45 [1985]). The embryonic stem cell line ES-D3 (ATCC No. CRL 1934) was maintained in an undifferentiated state in a medium containing LIF (Williams et al., *Nature*, 336: 684–687 [1988]). This medium contained D-MEM (high glucose), 1% glutamine, 0.1 mM 2-mercaptoethanol, penicillin-streptomycin, 15% heat-inactivated fetal bovine serum, and 15 ng/mL mouse LIF. When these cells were put into suspension culture in the same medium without LIF and containing 20% heat-inactivated fetal bovine serum (day 0), they aggregated and differentiated into multicellular structures called embryoid bodies. By day 8 of culture, beating primordial heart-like structures formed on a fraction of the bodies. The embryoid bodies were evaluated for the production of CHF activity by changing the differentiating ES cells to serum-free medium (D-MEM/F-12, 1% glutamine, penicillin-streptomycin, containing 0.03% bovine serum albumin) for a 24-hour accumulation. Prior to assay, the conditioned medium was concentrated 10 fold with a 3-K ultrafiltration membrane (Amicon), and dialyzed against assay medium. Medium conditioned for 24 hours starting at day 3 gave a hypertrophy score of 4.5–5.5, and starting at day 6 a score of 5.5–7.5.

A cDNA library in the plasmid expression vector, pRK5B (Holmes et al., *Science*, 253: 1278–1280 [1991]), was prepared following a vector priming strategy (Strathdee et al., *Nature*, 356: 763–767 [1992]). The vector, pRK5B, was linearized at the NotI site, treated with alkaline phosphatase, and ligated to the single-stranded oligonucleotide, ocdl.1.3, having the sequence: 5'-GCGGCCGCGAGCTCGAATTCTTTTTTTTTTTTTTTTTTTTTTTTTTTTTT (SEQ ID NO: 5). The ligated product was then cut with BstXI, and the 4700-bp vector fragment was isolated by agarose gel electrophoresis. The vector was further purified by oligo dA chromatography.

The expression library was constructed using 1 μg of the poly (A)$^+$ RNA, 5 μg of vector primer, and reagents from Amersham. Following first- and second-strand synthesis and T4 DNA polymerase fill-in reactions, the material was sized for inserts of greater than 500 bp by gel electrophoresis and circularized by blunt-end ligation without the addition of linkers. The ligations were used to transform E. coli strain DHα by electroporation. From 1 µg of poly(A)⁺ RNA, 499 ng of double-stranded cDNA were generated. Seventeen nanograms of cDNA were ligated, and 3.3 ng were transformed to yield 780,000 clones, 83% of which had inserts with an average size of 1470 bp.

DNA was isolated from pools of 75–15,000 clones and transfected into human embryonic kidney 293 cells by Lipofectamine transfection (Gibco BRL). Two micrograms of DNA were used to transfect ~200,000 cells in 6-well dishes. The cells were incubated in 2 mL of serum-free assay medium for four days. This medium consisted of 100 mL D-MEM/F-12, 100 µL transferrin (10 mg/mL), 20 µL insulin (5 mg/mL), 50 µL aprotinin (2 mg/mL), 1 mL pen/strep (JRH Biosciences No. 59602–77P), and 1 mL L-glutamine (200 mM). Transfection and expression efficiency was monitored by the inclusion of 0.2 µg of DNA for a plasmid expressing a secreted form of alkaline phosphatase (Tate et al., *FASEB J.*, 4: 227–231 [1990]).

One hundred microliters of conditioned culture medium from each transfected pool was assayed for hypertrophy in a final volume of 200 µL. For some pools the conditioned medium was concentrated 4–5 fold before assay with Centricon 3™ microconcentrators (Amicon). Ninety pools of 10,000–15,000 clones, 359 pools of 1000–5800 clones, and 723 pools of 75–700 clones were transfected and assayed for hypertrophy activity. Of these 1172 pools, two were found to be positive. Pool 437 (a pool of 187 clones) and pool 781 (a pool of 700 clones) gave scores of 4. A pure clone (designated pchf.437.48) from pool 437 was isolated by retransfection of positive pools containing fewer and fewer numbers of clones until a single clone was obtained. A pure clone from pool 781 (designated pchf.781) was isolated by colony hybridization to the insert from clone pchf.437.48.

The sequence for the insert of clone pchf.781 is provided in FIG. 1 (SEQ ID NOS: 1, 2, and 3 for the two nucleotide strands and amino acid sequence, respectively). The sequence of the insert of clone pchf.437.48 matches clone 781 starting at base 27 (underlined).

The first open reading frame of clone pchf.781 (see translation, FIG. 1) encodes a protein of 203 amino acids (translated MW=21.5 kDa). This protein contains one cysteine residue, one potential N-linked glycosylation site, and no hydrophobic N-terminal secretion signal sequence. The 3' untranslated region of clone pchf.781 contains a common mouse repeat known as b1 (bp ~895–1015). Hybridization of 7-day embryoid body poly(A)⁺ RNA with a probe from clone pchf.781 shows a single band of ~1.4 kb, which is about the same size as the insert from the cDNA clones.

The encoded sequence is not highly similar (>35% amino acid identity) to any known protein sequences. It does, however, show a low degree of similarity to a family of distantly related proteins including CNTF, interleukin-6 (IL-6), interleukin-11 (IL-11), LIF, and oncostatin M (OSM) (Bazan, *Neuron*, 7: 197–208 [1991]). CHF has 24% amino acid identity with mouse LIF (Rose and Todaro, WO 93/05169) and 21% amino acid identity with human CNTF (McDonald et al., *Biochim. Biophys. Acta*, 1090: 70–80 [1991]). See FIG. 2 for an alignment of CHF and human CNTF sequences. CNTF, IL-6, IL-11, LIF, and OSM use related receptor signaling proteins including gp130 that are members of the GH/cytokine receptor family (Kishimoto et al., *Cell*, 76: 253–262 [1994]). CNTF, like CHF, lacks an N-terminal secretion signal sequence.

C. Identity and Activity of Clone

To demonstrate that clone pchf.781 encodes a cardiac hypertrophy factor, expression studies were performed both by transfection of 293 cells and by utilizing a coupled in vitro SP6 transcription/translation system. ³⁵S-methionine and cysteine labeling of the proteins produced by pchf.781-transfected 293 cells (in comparison with vector-transfected cells) showed that the conditioned medium contained a labeled protein of about 21.8 kDa, and that the cell extract showed a protein of 22.5 kDa. Conditioned media from these transfections gave a morphology score of 6 when assayed for cardiac hypertrophy at a dilution of 1:4 using the assay described above. Conditioned media from unlabeled transfections gave a morphology score of 5.5–6.5 at a dilution of 1:1.

These assays were also positive for a second measure of cardiac hypertrophy—ANP release. See FIG. 3. This assay was performed by determination of the competition for the binding of ¹²⁵I-rat ANP for a rat ANP receptor A-IgG fusion protein. This method is similar to that used for the determination of gp120 using a CD4-IgG fusion protein (Chamow et al., *Biochemistry*, 29: 9885–9891 [1990]). Briefly, microtiter wells were coated with 100 µL of rat anti-human IgG antibody (2 µg/mL) overnight at 4° C. After washing with phosphate-buffered saline containing 0.5% bovine serum albumin, the wells were incubated with 100 µL of 3 ng/mL rat ANP receptor A-IgG (produced and purified in a manner analogous to the human ANP receptor A-IgG (Bennett et al., *J. Biol. Chem.*, 266: 23060–23067 [1991]) for one hour at 24° C. The wells were washed and incubated with 50 µL of rat ANP standard or sample for one hour at 24° C. Then 50 µL of ¹²⁵I-rat ANP (Amersham) was added for an additional one-hour incubation. The wells were washed and counted to determine the extent of binding competition. ANP concentrations in the samples were determined by comparison to a rat ANP standard curve.

³⁵S-methionine labeling of the proteins made by SP6-coupled in vitro transcription/translation (materials from Promega) of clone pchf.781 showed a labeled protein of 22.4 kDa. The labeled translation product was active when assayed for cardiac hypertrophy at a dilution of 1:200 (morphology score 5–6). To verify that the 22.4-kDa-labeled band was responsible for the hypertrophy activity, the labeled translation product was applied to a reverse-phase C4 column (Synchropak RO-4-4000) equilibrated in 10% acetonitrile 0.1% TFA, and eluted with an acetonitrile gradient. Coincident peaks of labeled protein and hypertrophy activity eluted from this column at ~55% acetonitrile.

A cardiac myocyte hypertrophy activity has been reported and partially purified from rat cardiac fibroblasts. Long et al., supra. To investigate further the identity of the CHF herein, rat cardiac fibroblasts were cultured. Conditioned medium from these primary cultures does have cardiac hypertrophy in the in vitro neonatal rat heart hypertrophy assay herein. Blot hybridization of rat fibroblast mRNA isolated from these cultures shows a clear band of 1.4 kb when probed with a coding region fragment of clone pchf.781. (Hybridization was performed in 5×SSC, 20% formamide at 42° C. with a final wash in 0.2×SSC at 50° C.)

Additional cross-species RNA blots were performed to determine conditions for isolation of clones encoding the human form of the cardiac hypertrophy factor. Blot hybridization of human placental mRNA shows a clear band of 1.1 kb when probed with a fragment of clone pchf.781 (bp 504–785). (Hybridization was performed in 5×SSC, 20% formamide at 42° C. with a final wash in 1×SSC at 50° C.)

These data indicate that a human clone for the cardiac hypertrophy factor can be isolated by screening a human placental cDNA library with the mouse probe under these conditions.

D. Purification of Factor

The culture medium conditioned by cells transfected with clone pchf.781 or a human clone is adjusted to 1.5M NaCl and applied to a Toyopearl™ Butyl-650M column. The column is washed with 10 mM TRIS-HCl, pH 7.5, 1M NaCl, and the activity eluted with 10 mM TRIS-HCl, pH 7.5, 10 mM Zwittergent™ 3–10. The peak of activity is adjusted to 150 mM NaCl, pH 8.0, and applied to a MONO-Q Fast Flow column. The column is washed with 10 mM TRIS-HCl, pH 8.0, 150 mM NaCl, 0.1% octyl glucoside and activity is found in the flow-through through fraction. The active material is then applied to a reverse phase C4 column in 0.1% TFA, 10% acetonitrile, and eluted with a gradient of 0.1% TFA up to 80%. The activity fractionates at about 15–30 kDa on gel-filtration columns. It is expected that a chaotrope such as guanidine-HCl, is required for resolution and recovery.

EXAMPLE II

Testing for in vivo Hypertrophy Activity

A. Normal Rats

The purified CHF from Example I is tested in normal rats to observe its effect on cardiovascular parameters such as blood pressure, heart rate, systemic vascular resistance, contractility, force of heart beat, concentric or dilated hypertrophy, left ventricular systolic pressure, left ventricular mean pressure, left ventricular end-diastolic pressure, cardiac output, stroke index, histological parameters, ventricular size, wall thickness, etc.

B. Pressure-Overload Mouse Model

The purified CHF is also tested in the pressure-overload mouse model wherein the pulmonary artery is constricted, resulting in right ventricular failure.

C. RV Murine Dysfunctional Model

A retroviral murine model of ventricular dysfunction can be used to test the purified CHF, and the dP/dt, ejection fraction, and volumes can be assayed with the hypertrophy assay described above. In this model, the pulmonary artery of the mouse is constricted so as to generate pulmonary hypertrophy and failure.

D. Transgenic Mouse Model

Transgenic mice that harbor a muscle actin promoter-IGF-I fusion gene display cardiac and skeletal muscle hypertrophy, without evidence of myopathy or heart failure. Further, IGF-I-gene-targeted mice display defects in cardiac myogenesis (as well as skeletal) including markedly decreased expression of ventricular muscle contractile protein genes. The purified CHF is tested in these two models.

Additional genetic-based models of dilated cardiomyopathy and cardiac dysfunction, without necrosis, can be developed in transgenic and gene-targeted mice (MLC-ras mice; aortic banding of heterozygous IGF-I-deficient mice).

E. Post-Myocardial Infarction Rat Model

The purified CHF is also tested in a post-myocardial infarction rat model, which is predictive of human congestive heart failure in producing natriuretic peptide. Specifically, male Sprague-Dawley rats (Charles River Breeding Laboratories, Inc., eight weeks of age) are acclimated to the facility for at least one week before surgery. Rats are fed a pelleted rat chow and water ad libitum and housed in a light- and temperature-controlled room.

1. Coronary Arterial Ligation

Myocardial infarction is produced by left coronary arterial ligation as described by Greenen et al., *J. Appl. Physiol.*, 93: 92–96 (1987) and Buttrick et al., *Am. J. Physiol.*, 260: 11473–11479 (1991). The rats are anesthetized with sodium pentobarbital (60 mg/kg, intraperitoneally), intubated via tracheotomy, and ventilated by a respirator (Harvard Apparatus Model 683). After a left-sided thoracotomy, the left coronary artery is ligated approximately 2 mm from its origin with a 7-0 silk suture. Sham animals undergo the same procedure except that the suture is passed under the coronary artery and then removed. All rats are handled according to the "Position of the American Heart Association on Research Animal Use" adopted 11 Nov. 1984 by the American Heart Association. Four to six weeks after ligation, myocardial infarction could develop into heart failure in rats.

In clinical patients, myocardial infarction or coronary artery disease is the most common cause of heart failure. Congestive heart failure in this model reasonably mimics congestive heart failure in most human patients.

2. Electrocardiograms

One week after surgery, electrocardiograms are obtained under light metofane anesthesia to document the development of infarcts. The ligated rats of this study are subgrouped according to the depth and persistence of pathological Q waves across the precordial leads. Buttrick et al., supra; Kloner et al., *Am. Heart J.*, 51: 1009–1013 (1983). This provides a gross estimate of infarct size and assures that large and small infarcts are not differently distributed in the ligated rats treated with CHF or CHF antagonist and vehicle. Confirmation is made by precise infarct size measurement.

3. CHF or CHF Antagonist Administration

Four weeks after surgery, CHF or CHF antagonist (10 μg/kg to 10 mg/kg twice a day for 15 days) or saline vehicle is injected subcutaneously in both ligated rats and sham controls. Body weight is measured twice a week during the treatment. CHF or CHF antagonist is administered in saline or water as a vehicle.

4. Catheterization

After 13-day treatment with CHF, CHF antagonist, or vehicle, rats are anesthetized with pentobarbital sodium (50 mg/kg, intraperitoneally). A catheter (PE 10 fused with PE 50) filled with heparin-saline solution (50/U/mL) is implanted into the abdominal aorta through the right femoral artery for measurement of arterial pressure and heart rate. A second catheter (PE 50) is implanted into the right atrium through the right jugular vein for measurement of right atrial pressure and for saline injection. For measurement of left ventricular pressures and contractility (dP/dt), a third catheter (PE 50) is implanted into the left ventricle through the right carotid artery. For the measurement of cardiac output by a thermodilution method, a thermistor catheter (Lyons Medical Instrument Co., Sylmar, Calif.) is inserted into the aortic arch. The catheters are exteriorized at the back of the neck with the aid of a stainless-steel wire tunneled subcutaneously and then fixed. Following catheter implantation, all rats are housed individually.

5. Hemodynamic Measurements

One day after catherization, the thermistor catheter is processed in a microcomputer system (Lyons Medical Instrument Co.) for cardiac output determination, and the other three catheters are connected to a Model CP-10 pressure transducer (Century Technology Company, Inglewood, Calif.) coupled to a Grass Model 7 polygraph (Grass Instruments, Quincy, Mass.). Mean arterial pressure (MAP), systolic arterial pressure (SAP), heart rate (HR), right atrial pressure (RAP), left ventricular systolic pressure (LVSP), left ventricular mean pressure (LVMP), left ventricular end-diastolic pressure (LVEDP), and left ventricular maximum (dP/dt) are measured in conscious, unrestrained rats.

For measurement of cardiac output, 0.1 mL of isotonic saline at room temperature is injected as a bolus via the jugular vein catheter. The thermodilution curve is monitored by VR-16 simultrace recorders (Honeywell Co., N.Y.) and cardiac output (CO) is digitally obtained by the microcomputer. Stroke volume (SV)=CO/HR; Cardiac index (CI)=CO/BW; Systemic vascular resistance (SVR)=MAP/CI.

After measurement of these hemodynamic parameters, 1 mL of blood is collected through the arterial catheter. Serum is separated and stored at $-70°$ C. for measurement of CHF levels or various biochemical parameters if desired.

At the conclusion of the experiments, the rats are anesthetized with pentobarbital sodium (60 mg/kg) and the heart is arrested in diastole with intra-atrial injection of KCl (1M). The heart is removed, and the atria and great vessels are trimmed from the ventricle. The ventricle is weighed and fixed in 10% buffered formalin.

All experimental procedures are approved by the Institutional Animal Care and Use Committee of Genentech, Inc. before initiation of the study.

6. Infarct Size Measurements

The right ventricular free wall is dissected from the left ventricle. The left ventricle is cut in four transverse slices from apex to base. Five micrometer sections are cut and stained with Massons' trichrome stain and mounted. The endocardial and epicardial circumferences of the infarcted and non-infarcted left ventricle are determined with a planimeter Digital Image Analyzer. The infarcted circumference and the left ventricular circumference of all four slices are summed separately for each of the epicardial and endocardial surfaces and the sums are expressed as a ratio of infarcted circumference to left ventricular circumference for each surface. These two ratios are then averaged and expressed as a percentage for infarct size.

7. Statistical Analysis

Results are expressed as mean±SEM. Two-way and one-way analysis of variance (ANOVA) is performed to assess differences in parameters among groups. Significant differences are then subjected to post hoc analysis using the Newman-Keuls method. $p<0.05$ is considered significant.

8. Results

The mean body weight before and after treatment with CHF or CHF antagonist or vehicle is not expected to be different among the experimental groups. Infarct size in ligated rats is not expected to differ between the vehicle-treated group and the CHF- or CHF-antagonist-treated group.

It is expected that administration of CHF or CHF antagonist to the ligated rats in the doses set forth above would result in improved cardiac hypertrophy by increasing ventricular contractility and decreasing peripheral vascular resistance over that observed with the vehicle-treated sham and ligated rat controls. This expected result would demonstrate that administration of CHF or CHF antagonist improves cardiac function in congestive heart failure. In sham rats, however, CHF or CHF antagonist administration at this dose is not expected to alter significantly cardiac function except possibly slightly lowering arterial pressure and peripheral vascular resistance.

It would be reasonably expected that the rat data herein may be extrapolated to horses, cows, humans, and other mammals, correcting for the body weight of the mammal in accordance with recognized veterinary and clinical procedures. Using standard protocols and procedures, the veterinarian or clinician will be able to adjust the doses, scheduling, and mode of administration of CHF or a CHF antagonist to achieve maximal effects in the desired mammal being treated. Humans are believed to respond in this manner as well.

EXAMPLE III

Proposed Clinical Treatment of Dilated Cardiomyopathy

A. Intervention

Patient self-administration of CHF or CHF antagonist at an initial dose of 10–150 μg/kg/day is proposed. The dose would be adjusted downward for adverse effects. If no beneficial effects and no limiting adverse effects are determined at the time of re-evaluation, the dose would be adjusted upward. Concurrent medication doses (e.g., Captopril™ brand ACE inhibitor and diuretics) would be adjusted at the discretion of the study physician. After the maximum dose is administered for 8 weeks, the CHF or CHF antagonist administration is stopped, and re-evaluation is performed after a similar time period off treatment (or a placebo).

B. Inclusion Criteria

Patients would be considered for the study if they meet the following criteria:

Dilated cardiomyopathy (DCM). Idiopathic DCM, or ischemic DCM without discrete areas of akinesis/dyskinesis of the left ventricle (LV) on contrast ventriculography or 2D echocardiography. Evidence for impaired systolic function to include either LV end-diastolic dimension (EDD)>3.2 $cm/m^2$ BSA or EDV>82 $mL/m^2$ on 2D echocardiography, LV fractional shortening<28% on echocardiography, or ejection fraction (by contrast ventriculography or radionuclide angiography)<0.49.

Symptoms. New York Heart Association class III or peak exercise $VO_2$<16 mL/kg/min. (adjusted for age), stable for at least one month on digoxin, diuretics, and vasodilators (ACE inhibitors).

Concurrent ACE inhibitor therapy.

Adequate echocardiographic "windows" to permit assessment of left ventricular volume and mass.

Ability to self-administer CHF or CHF antagonist according to the dosage schedule, and to return reliably for follow-up assessments.

Consent of patient and patient's primary physician to participate.

Absence of exclusion criteria.

C. Exclusion Criteria

Patients would be excluded from consideration for any of the following reasons:

Dilated cardiomyopathy resulting from valvular heart disease (operable or not), specific treatable etiologies (including alcohol, if abstinence has not been attempted), or operable coronary artery disease.

Exercise limited by chest pain or obstructive peripheral vascular disease.

Chronic obstructive lung disease.

Diabetes mellitus or impaired glucose tolerance.

History of carpal tunnel syndrome, or evidence for positive Tinel's sign on examination.

History of kidney stones.

Symptomatic osteoarthritis.

Inability to consent for or participate in serial bicycle ergometry with invasive hemodynamic monitoring (as described below).

Active malignancy.

D. Patient Assessment

1) Major Assessment Points: baseline; after peak stable CHF or CHF antagonist dose maintained for 8 weeks; after equal period after drug discontinuation.

It is anticipated that patients would remain in the hospital for two to three days at the onset of active treatment, with daily weights and laboratory data including electrolytes, phosphorus, BUN, creatinine, and glucose. Following this, they would be monitored on the Clinical Research Center floor daily for an additional two to three days.

i. Physical examination.

ii. Symptom Point Score (Kelly et al., *Amer. Heart J.*, 119: 1111 [1990]).

iii. Laboratory data: CBC; electrolytes (including $Mg^{+2}$ and $Ca^{+2}$); BUN; creatinine; phosphorus; fasting glucose and lipid profile (total cholesterol, HDL-C, LDL-C, triglycerides); liver function tests (AST, ALT, alkaline phosphatase, total bilirubin); total protein; albumin; uric acid; and CHF.

iv. 2D, M-mode, and doppler echocardiography, including: diastolic and systolic dimensions at the papillary muscle level; ejection fraction estimate by area planimetry from apical 2-chamber and 4-chamber views, estimated systolic and diastolic volumes by Simpson's rule method, and estimated left ventricular mass; doppler assessment of mitral valve inflow profile (IVRT, peak E, peak A, deceleration time, A wave duration), and pulmonary vein flow profile (systolic flow area, diastolic flow area, A reversal duration, and velocity).

v. Rest and exercise hemodynamics and measured oxygen consumption, using bicycle ergometry with percutaneously inserted pulmonary artery and arterial catheters. Perceived exertion level would be scored on the Borg scale, and measurements of pulmonary artery systolic, diastolic, and mean pressures, as well as arterial pressures and pulmonary capillary wedge pressure would be measured at each increment of workload, along with arterial and mixed venous oxygen content for calculating cardiac output.

vi. Assessment of body fat and lean body mass, as well as skeletal muscle strength and endurance.

2) Interim Assessment Points: weekly i. Physical examination.

ii. Symptom Point Score.

iii. Laboratory data: electrolytes, BUN, creatinine, phosphorus, fasting glucose, somatomedin-C, and CHF.

E. Potential Benefits

1) Improved sense of well-being.
2) Increased exercise tolerance.
3) Increased muscle strength and lean body mass.
4) Decreased systemic vascular resistance.
5) Enhanced cardiac performance.
6) Enhanced compensatory myocardial hypertrophy.

EXAMPLE IV

Testing for in vitro Neurotrophic Activity

An assay used for ciliary ganglion neurotrophic activity was performed as described in Leung, *Neuron*, 8: 1045–1053 (1992). Briefly, ciliary ganglia were dissected from E7-E8 chick embryos and dissociated in trypsin-EDTA (Gibco 15400-013) diluted ten fold in phosphate-buffered saline for 15 minutes at 37° C. The ganglia were washed free of trypsin with three washes of growth medium (high glucose D-MEM supplemented with 10% fetal bovine serum, 1.5 mM glutamine, 100 µg/mL penicillin, and 100 µg/mL strepomycin), and then gently triturated in 1 mL of growth medium into a single-cell suspension. Neurons were enriched by plating this cell mixture in 5 mL of growth media onto a 100-mm tissue culture dish for 4 hours at 37° C. in a tissue culture incubator. During this time the non-neuronal cells preferentially stuck to the dish and neurons were gently washed free at the end of the incubation.

The enriched neurons were then plated into a 96-well plate previously coated with collagen. In each well, 1000 to 2000 cells were plated, in a final volume of 100 to 250 µL, with dilutions of the conditioned medium from the pchf.781-transfected 293 cells of Example I. The cells were also plated with the transfected 293 conditioned medium as a control, and with a CNTF standard as a comparison. Following a 2–4-day incubation at 37° C., the number of live cells was assessed by staining live cells using the vital dye metallothionine (MTT). One-fifth of the volume of 5 mg/mL MTT (Sigma M2128) was added to the wells. After a 2–4-hour incubation at 37° C., live cells (filled with a dense purple precipitate) were counted by phase microscopy at 100× magnification.

Figure 4:
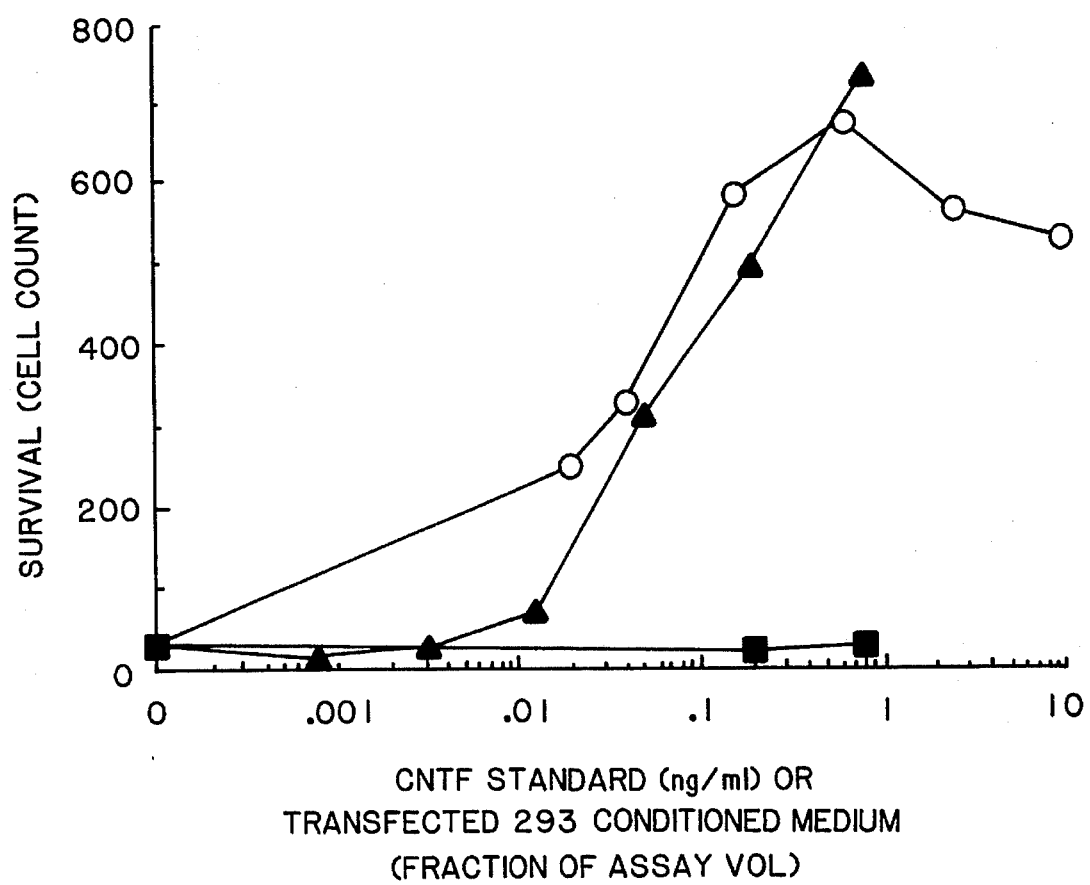
FIG. 4 shows a graph of survival of live ciliary ganglion neurons (measured by cell count) as a function of either the ciliary neutrotrophic factor (CNTF) standard (in ng/mL) or the transfected 293 conditioned medium (in fraction of assay volume), using a CNTF standard (circles), medium from a CHF DNA transfection of 293 cells (triangles), and medium from a control DNA transfection of 293 cells (squares).

The results of the assay are shown in FIG. 4. It can be seen that the pchf.781 transfection (triangles) increased survival of the live neurons (measured by cell count) as the fraction of assay volume of transfected 293 conditioned medium increased. This is similar to the pattern for the CNTF standard (circles), and is in contrast to the control transfection (squares), which showed no increase in survival as a function of increased fraction of assay volume of conditioned medium. This indicates that CHF is useful as a neurotrophic agent, having a similar effect to that observed with CNTF.

---

What is claimed is:

1. Isolated CHF having the translated CHF amino acid sequence (SEQ ID NO: 3) shown in FIG. 1.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1352 bases
        ( B ) TYPE: nucleic acid (C) STRANDEDNESS: single
(D) TOPOLOGY: linear (xi) SEQUENCE DESCRIPTION: SEQ ID NO:1:

| | | | | | |
|---|---|---|---|---|---|
| GGATAAGCCT | GGGGCCAGCA | TGAGCCAGAG | GGAGGGAAGT | CTGGAAGACC | 50 |
| ACCAGACTGA | CTCCTCAATC | TCATTCCTAC | CCCATTTGGA | GGCCAAGATC | 100 |
| CGCCAGACAC | ACAACCTTGC | CCGCCTCCTG | ACCAAATATG | CAGAACAACT | 150 |
| TCTGGAGGAA | TACGTGCAGC | AACAGGGAGA | GCCCTTTGGG | CTGCCGGGCT | 200 |
| TCTCACCACC | GCGGCTGCCG | CTGGCCGGCC | TGAGTGGCCC | GGCTCCGAGC | 250 |
| CATGCAGGGC | TACCGGTGTC | CGAGCGGCTG | CGGCAGGATG | CAGCCGCCCT | 300 |
| GAGTGTGCTG | CCCGCGCTGT | GGATGCCGT | CCGCCGCCGC | CAGGCGGAGC | 350 |
| TGAACCCGCG | CGCCCCGCGC | CTGCTGCGGA | GCCTGGAGGA | CGCAGCCCGC | 400 |
| CAGGTTCGGG | CCCTGGGCGC | CGCGGTGGAG | ACAGTGCTGG | CCGCGCTGGG | 450 |
| CGCTGCAGCC | CGCGGGCCCG | GGCCAGAGCC | CGTCACCGTC | GCCACCCTCT | 500 |
| TCACGGCCAA | CAGCACTGCA | GGCATCTTCT | CAGCCAAGGT | GCTGGGGTTC | 550 |
| CACGTGTGCG | GCCTCTATGG | CGAGTGGGTG | AGCCGCACAG | AGGGCGACCT | 600 |
| GGGCCAGCTG | GTGCCAGGGG | CGTCGCCTG | AGAGTGAATA | CTTTTTCTTG | 650 |
| TAAGCTCGCT | CTGTCTCGCC | TCTTTGGCTT | CAAATTTTCT | GTCTCTCCAT | 700 |
| CTGTGTCCTG | TGTGTTCTTG | GGCTGTCCCT | ATCTTTCTGC | ATTTGTGTGG | 750 |
| TCTCTCTCTT | CTGCTCTCCT | CTCTGCAGGG | AGCTTCTTTT | TTCCAACAGT | 800 |
| TTCTCGTTTT | GTCTCTCTCC | AGTCTTGAAC | ACTTTGTCT | CCGAGAGGTC | 850 |
| TCTTTTTGTT | TCCTTGTCTC | TTGGTTCTTT | CTTTGCTTGC | TTGCTTGCTT | 900 |
| GCTTGCTTGT | TGTTGAGACA | GGGTCTCACC | ATATAGCTCT | GGATGGCCTG | 950 |
| GAACTTGCTA | TGTAGGCCAG | GCTGGCCTCC | AGCTCATAGA | GATCCACTTG | 1000 |
| CCTCCGACTC | CCAATTTCCC | CATCTGTCTC | CCTGTGATCC | ATATGGGTAT | 1050 |
| GTGTAACCCT | TACTTTGTCT | CATGGAGGTG | ACAATTTTTC | TCCCTTCAGT | 1100 |
| TTCTTTGTTC | TTTACTGACC | AGAAAAGTGC | CTACTTGTCC | CCTGGTGGCA | 1150 |
| AGGCCATTCA | CCTTAGGACC | TTCCCACCAG | TTCCTTTGTA | GGCAAATCCC | 1200 |
| TCCCCCTTTG | AGGTCCTTCC | CTTTCATACC | GCCCTAGGCT | GGTCAATGGA | 1250 |
| GAGAGAAAGG | CAGAAAAACA | TCTTTAAAGA | GTTTTATTTG | AGAATAAATT | 1300 |
| AATTTTTGTA | AATAAAATGT | TTAACAATAA | AACTAAACTT | TTATGAAAAA | 1350 |
| AA | | | | | 1352 |

(2) INFORMATION FOR SEQ ID NO:2:

(i) SEQUENCE CHARACTERISTICS:
(A) LENGTH: 1352 bases
(B) TYPE: nucleic acid
(C) STRANDEDNESS: single
(D) TOPOLOGY: linear (xi) SEQUENCE DESCRIPTION: SEQ ID NO:2:

| | | | | | |
|---|---|---|---|---|---|
| CCTATTCGGA | CCCCGGTCGT | ACTCGGTCTC | CCTCCCTTCA | GACCTTCTGG | 50 |
| TGGTCTGACT | GAGGAGTTAG | AGTAAGGATG | GGTAAACCT | CCGGTTCTAG | 100 |
| GCGGTCTGTG | TGTTGGAACG | GGCGGAGGAC | TGGTTTATAC | GTCTTGTTGA | 150 |
| AGACCTCCTT | ATGCACGTCG | TTGTCCCTCT | CGGGAAACCC | GACGGCCCGA | 200 |

| AGAGTGGTGG | CGCCGACGGC | GACCGGCCGG | ACTCACCGGG | CCGAGGCTCG | 250 |
| GTACGTCCCG | ATGGCCACAG | GCTCGCCGAC | GCCGTCCTAC | GTCGGCGGGA | 300 |
| CTCACACGAC | GGGCGCGACA | ACCTACGGCA | GGCGGCGGCG | GTCCGCCTCG | 350 |
| ACTTGGGCGC | GCGGGGCGCG | GACGACGCCT | CGGACCTCCT | GCGTCGGGCG | 400 |
| GTCCAAGCCC | GGGACCCGCG | GCGCCACCTC | TGTCACGACC | GGCGCGACCC | 450 |
| GCGACGTCGG | GCGCCCGGGC | CCGGTCTCGG | GCAGTGGCAG | CGGTGGGAGA | 500 |
| AGTGCCGGTT | GTCGTGACGT | CCGTAGAAGA | GTCGGTTCCA | CGACCCCAAG | 550 |
| GTGCACACGC | CGGAGATACC | GCTCACCCAC | TCGGCGTGTC | TCCCGCTGGA | 600 |
| CCCGGTCGAC | CACGGTCCCC | CGCAGCGGAC | TCTCACTTAT | GAAAAGAAC | 650 |
| ATTCGAGCGA | GACAGAGCGG | AGAAACCGAA | GTTTAAAAGA | CAGAGAGGTA | 700 |
| GACACAGGAC | ACACAAGAAC | CCGACAGGGA | TAGAAAGACG | TAAACACACC | 750 |
| AGAGAGAGAA | GACGAGAGGA | GAGACGTCCC | TCGAAGAAAA | AAGGTTGTCA | 800 |
| AAGAGCAAAA | CAGAGAGAGG | TCAGAACTTG | TGAAAACAGA | GGCTCTCCAG | 850 |
| AGAAAAACAA | AGGAACAGAG | AACCAAGAAA | GAAACGAACG | AACGAACGAA | 900 |
| CGAACGAACA | ACAACTCTGT | CCCAGAGTGG | TATATCGAGA | CCTACCGGAC | 950 |
| CTTGAACGAT | ACATCCGGTC | CGACCGGAGG | TCGAGTATCT | CTAGGTGAAC | 1000 |
| GGAGGCTGAG | GGTTAAAGGG | GTAGACAGAG | GGACACTAGG | TATACCCATA | 1050 |
| CACATTGGGA | ATGAAACAGA | GTACCTCCAC | TGTTAAAAAG | AGGGAAGTCA | 1100 |
| AAGAAACAAG | AAATGACTGG | TCTTTTCACG | GATGAACAGG | GGACCACCGT | 1150 |
| TCCGGTAAGT | GGAATCCTGG | AAGGGTGGTC | AAGGAAACAT | CCGTTTAGGG | 1200 |
| AGGGGGAAAC | TCCAGGAAGG | GAAAGTATGG | CGGGATCCGA | CCAGTTACCT | 1250 |
| CTCTCTTTCC | GTCTTTTTGT | AGAAATTTCT | CAAAATAAAC | TCTTATTTAA | 1300 |
| TTAAAAACAT | TTATTTTACA | AATTGTTATT | TTGATTTGAA | AATACTTTTT | 1350 |
| TT | | | | | 1352 |

( 2 ) INFORMATION FOR SEQ ID NO:3:

( i ) SEQUENCE CHARACTERISTICS:
        ( A ) LENGTH: 203 amino acids
        ( B ) TYPE: amino acid
        ( D ) TOPOLOGY: linear ( x i ) SEQUENCE DESCRIPTION: SEQ ID NO:3:

```
Met  Ser  Gln  Arg  Glu  Gly  Ser  Leu  Glu  Asp  His  Gln  Thr  Asp  Ser
 1                 5                    10                       15

Ser  Ile  Ser  Phe  Leu  Pro  His  Leu  Glu  Ala  Lys  Ile  Arg  Gln  Thr
                 20                      25                       30

His  Asn  Leu  Ala  Arg  Leu  Leu  Thr  Lys  Tyr  Ala  Glu  Gln  Leu  Leu
                 35                      40                       45

Glu  Glu  Tyr  Val  Gln  Gln  Gly  Glu  Pro  Phe  Gly  Leu  Pro  Gly
                 50                      55                       60

Phe  Ser  Pro  Pro  Arg  Leu  Pro  Leu  Ala  Gly  Leu  Ser  Gly  Pro  Ala
                 65                      70                       75

Pro  Ser  His  Ala  Gly  Leu  Pro  Val  Ser  Glu  Arg  Leu  Arg  Gln  Asp
                 80                      85                       90

Ala  Ala  Ala  Leu  Ser  Val  Leu  Pro  Ala  Leu  Leu  Asp  Ala  Val  Arg
                 95                     100                      105

Arg  Arg  Gln  Ala  Glu  Leu  Asn  Pro  Arg  Ala  Pro  Arg  Leu  Leu  Arg
```

|     |     |     |     |     |     |     |     | 1 1 0 |     |     |     | 1 1 5 |     |     |     | 1 2 0 |
|---|---|---|---|---|---|---|---|---|---|---|---|---|---|---|---|---|

Ser Leu Glu Asp Ala Ala Arg Gln Val Arg Ala Leu Gly Ala Ala
                    125                 130                 135

Val Glu Thr Val Leu Ala Ala Leu Gly Ala Ala Ala Arg Gly Pro
                    140                 145                 150

Gly Pro Glu Pro Val Thr Val Ala Thr Leu Phe Thr Ala Asn Ser
                    155                 160                 165

Thr Ala Gly Ile Phe Ser Ala Lys Val Leu Gly Phe His Val Cys
                    170                 175                 180

Gly Leu Tyr Gly Glu Trp Val Ser Arg Thr Gly Asp Leu Gly
                    185                 190                 195

Gln Leu Val Pro Gly Gly Val Ala
                    200         203

( 2 ) INFORMATION FOR SEQ ID NO:4:

( i ) SEQUENCE CHARACTERISTICS:
    ( A ) LENGTH: 200 amino acids
    ( B ) TYPE: amino acid
    ( D ) TOPOLOGY: linear ( x i ) SEQUENCE DESCRIPTION: SEQ ID NO:4:

Met Ala Phe Thr Glu His Ser Pro Leu Thr Pro His Arg Arg Asp
 1               5                 10                  15

Leu Cys Ser Arg Ser Ile Trp Leu Ala Arg Lys Ile Arg Ser Asp
                    20                  25                  30

Leu Thr Ala Leu Thr Glu Ser Tyr Val Lys His Gln Gly Leu Asn
                    35                  40                  45

Lys Asn Ile Asn Leu Asp Ser Ala Asp Gly Met Pro Val Ala Ser
                    50                  55                  60

Thr Asp Gln Trp Ser Glu Leu Thr Glu Ala Glu Arg Leu Gln Glu
                    65                  70                  75

Asn Leu Gln Ala Tyr Arg Thr Phe His Val Leu Leu Ala Arg Leu
                    80                  85                  90

Leu Glu Asp Gln Gln Val His Phe Thr Pro Thr Glu Gly Asp Phe
                    95                  100                 105

His Gln Ala Ile His Thr Leu Leu Leu Gln Val Ala Ala Phe Ala
                    110                 115                 120

Tyr Gln Ile Glu Glu Leu Met Ile Leu Leu Glu Tyr Lys Ile Pro
                    125                 130                 135

Arg Asn Glu Ala Asp Gly Met Pro Ile Asn Val Gly Asp Gly Gly
                    140                 145                 150

Leu Phe Glu Lys Lys Leu Trp Gly Leu Lys Val Leu Gln Glu Leu
                    155                 160                 165

Ser Gln Trp Thr Val Arg Ser Ile His Asp Leu Arg Phe Ile Ser
                    170                 175                 180

Ser His Gln Thr Gly Ile Pro Ala Arg Gly Ser His Tyr Ile Ala
                    185                 190                 195

Asn Asn Lys Lys Met
                    200

( 2 ) INFORMATION FOR SEQ ID NO:5:

( i ) SEQUENCE CHARACTERISTICS:
    ( A ) LENGTH: 50 bases
    ( B ) TYPE: nucleic acid
    ( C ) STRANDEDNESS: single
    ( D ) TOPOLOGY: linear ( x i ) SEQUENCE DESCRIPTION: SEQ ID NO:5:

GCGGCCGCGA GCTCGAATTC TTTTTTTTTT TTTTTTTTTT TTTTTTTTTT 50